(12) United States Patent
Park et al.

(10) Patent No.: US 10,441,623 B2
(45) Date of Patent: Oct. 15, 2019

(54) DIETARY COMPOSITION AND METHOD FOR PREVENTING, REDUCING, ALLEVIATING OR TREATING IDIOPATHIC VOMITING

(71) Applicant: Mars, Incorporated, McLean, VA (US)

(72) Inventors: Jean Soon Park, Cincinnati, OH (US); Ping Hu, Mason, OH (US); Yakang Lin, Liberty Township, OH (US); Lori Ann Reinsalu, Cincinnati, OH (US)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 14/198,662

(22) Filed: Mar. 6, 2014

(65) Prior Publication Data

US 2014/0271943 A1 Sep. 18, 2014

Related U.S. Application Data

(60) Provisional application No. 61/786,465, filed on Mar. 15, 2013.

(51) Int. Cl.

| | | |
|---|---|---|
| A61K 45/06 | (2006.01) |
| A61K 36/9066 | (2006.01) |
| A61K 36/484 | (2006.01) |
| A61K 36/889 | (2006.01) |
| A61K 36/752 | (2006.01) |
| A61K 36/77 | (2006.01) |
| A61K 36/81 | (2006.01) |
| A61K 36/82 | (2006.01) |
| A61K 36/835 | (2006.01) |
| A61K 36/87 | (2006.01) |
| A61K 36/88 | (2006.01) |
| A61K 36/9068 | (2006.01) |
| A61K 36/00 | (2006.01) |
| A61K 36/15 | (2006.01) |
| A61K 36/16 | (2006.01) |
| A61K 36/185 | (2006.01) |
| A61K 36/19 | (2006.01) |
| A61K 36/23 | (2006.01) |
| A61K 36/28 | (2006.01) |
| A61K 36/324 | (2006.01) |
| A61K 36/41 | (2006.01) |
| A61K 36/45 | (2006.01) |
| A61K 36/47 | (2006.01) |
| A61K 36/48 | (2006.01) |
| A61K 36/53 | (2006.01) |
| A61K 36/54 | (2006.01) |
| A61K 36/55 | (2006.01) |
| A61K 36/61 | (2006.01) |
| A61K 36/634 | (2006.01) |
| A61K 36/67 | (2006.01) |
| A61K 36/708 | (2006.01) |
| A61K 36/718 | (2006.01) |
| A61K 36/736 | (2006.01) |

(52) U.S. Cl.
CPC .......... *A61K 36/9066* (2013.01); *A61K 36/00* (2013.01); *A61K 36/15* (2013.01); *A61K 36/16* (2013.01); *A61K 36/185* (2013.01); *A61K 36/19* (2013.01); *A61K 36/23* (2013.01); *A61K 36/28* (2013.01); *A61K 36/324* (2013.01); *A61K 36/41* (2013.01); *A61K 36/45* (2013.01); *A61K 36/47* (2013.01); *A61K 36/48* (2013.01); *A61K 36/484* (2013.01); *A61K 36/53* (2013.01); *A61K 36/54* (2013.01); *A61K 36/55* (2013.01); *A61K 36/61* (2013.01); *A61K 36/634* (2013.01); *A61K 36/67* (2013.01); *A61K 36/708* (2013.01); *A61K 36/718* (2013.01); *A61K 36/736* (2013.01); *A61K 36/752* (2013.01); *A61K 36/77* (2013.01); *A61K 36/81* (2013.01); *A61K 36/82* (2013.01); *A61K 36/835* (2013.01); *A61K 36/87* (2013.01); *A61K 36/88* (2013.01); *A61K 36/889* (2013.01); *A61K 36/9068* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,203,797 B1 | 3/2001 | Perry | |
| 6,348,502 B1 | 2/2002 | Gardiner et al. | |
| 6,359,017 B1 | 3/2002 | Bruckner et al. | |
| 6,403,142 B1 | 6/2002 | McDaniel et al. | |
| 6,579,542 B1 * | 6/2003 | Faulkner | 424/726 |
| 7,687,077 B2 | 3/2010 | Khoo | |
| 7,722,905 B2 | 5/2010 | Khoo | |

(Continued)

FOREIGN PATENT DOCUMENTS

| | | |
|---|---|---|
| CN | 1337244 A | 2/2002 |
| CN | 1686280 | 10/2005 |

(Continued)

OTHER PUBLICATIONS 2015 http://www.mayoclinic.org/symptoms/nausea/basics/causes/sym-20050736.*
2015 http://www.webmd.com/digestive-disorders/digestive-diseases-nausea-vomiting.*
Rasatara, 1979, Ed.11th, reprinted—Delhi 2000, pp. 288-289.*
Suthar et al., "A Review on Ginger: Pre-Clinical and Clinical Trials," Indian Journal of Traditional Knowledge, Resources, New Delhi, New Delhi—India, vol. 2, No. 1, pp. 51-61, Jan. 1, 2003.
Sharma et al., "Antiemetic Efficacy of Ginger Against Cisplatin-Induced Emesis in Dogs", Journal of Ethnopharmacology, vol. 57, No. 2, pp. 93-96, 1997, Abstract.

(Continued)

*Primary Examiner* — Terry A McKelvey
*Assistant Examiner* — Catheryne Chen
(74) *Attorney, Agent, or Firm* — Mars, Incorporated

(57) ABSTRACT

The present invention relates to compositions containing plant materials or extracts with inhibitory effect on a 5-HT3a and/or NK-1 receptor for preventing or treating idiopathic vomiting.

6 Claims, 33 Drawing Sheets

(56) References Cited

U.S. PATENT DOCUMENTS

| | | | |
|---|---|---|---|
| 7,867,540 | B2 | 1/2011 | Didzbalis et al. |
| 2003/0194423 | A1 | 10/2003 | Torney et al. |
| 2006/0008511 | A1 | 1/2006 | Lin et al. |
| 2006/0111307 | A1 | 5/2006 | Robbins |
| 2006/0200320 | A1* | 9/2006 | Al-Murrani ......... G06F 19/3475 702/20 |
| 2008/0241226 | A1 | 10/2008 | Abelin et al. |
| 2009/0076053 | A1 | 3/2009 | Robbins |
| 2011/0135724 | A1 | 6/2011 | Venkatesh |
| 2011/0159500 | A1 | 6/2011 | Khoo et al. |
| 2011/0311684 | A1 | 12/2011 | Rea |
| 2012/0294954 | A1 | 11/2012 | Khoo et al. |
| 2012/0329736 | A1 | 12/2012 | Huang et al. |
| 2014/0271949 | A1 | 9/2014 | Park |

FOREIGN PATENT DOCUMENTS

| | | | |
|---|---|---|---|
| CN | 101 721 675 | A | 6/2010 |
| CN | 101829307 | A * | 9/2010 |
| CN | 101 874 894 | A | 11/2010 |
| CN | 102133385 | A | 7/2011 |
| CN | 102166335 | A | 8/2011 |
| CN | 102 198 259 | A | 9/2011 |
| CN | 102217721 | A | 10/2011 |
| CN | 102283926 | A | 12/2011 |
| CN | 102 370 096 | A | 3/2012 |
| CN | 102 406 735 | A | 4/2012 |
| CN | 102 671 058 | A | 9/2012 |
| DE | 36 26 128 | A1 | 2/1988 |
| DE | 3626128 | | 2/1998 |
| EP | 2 366 292 | A1 | 9/2011 |
| JP | 09208858 | | 8/1997 |
| JP | 10158183 | | 6/1998 |
| JP | 2004359550 | | 12/2004 |
| JP | 2008163233 | A | 7/2008 |
| JP | 2010 0309633 | A | 2/2010 |
| KR | 20120118102 | A | 10/2012 |
| WO | WO 2008/65457 | | 6/2008 |

OTHER PUBLICATIONS

PCT International Search Report dated Jun. 10, 2014—6 pages.
PCT International Search Report dated May 6, 2014, 5 pgs PCT/US2014/018296.
"The Catsite", (2011, http://www.thecatsite.com/t/t229784/possible-night-time-vomiting-ibd-lymphoma-solution), 4 pgs.
Elwood, et al., "Emesis in Dogs: A Review", Journal of Small Animal Practice, vol. 51, No. 1, Jan. 2010, pp. 4-22.
Gidda, et al., "Antagonism of Serotonin-3 (5-HT-3) Receptors within the Blood-Brain Barrier Prevents Cisplatin-induced Emesis in Dogs", Journal of Pharmacology and Experimental Therapeutics, vol. 273, No. 2, Jan. 1, 1995, pp. 695-701.
Gullford, et al., "The Nutritional Management of Gastrointestinal Tract Disorders in Companion Animals", New Zealand Veterinary Journal, 51:6, pp. 284-291, 2003.
Navari, "A Review of the Prevention of Nausea and Vomiting Induced by Chemotherapy", European Oncology and Haematology, vol. 9, No. 1, Jan. 1, 2012, pp. 51-55.
Hsu, et al., "Clinicial Studies with Curcumin", In: Aggarwal, BB et al (eds) The Molecular Targets and Therapeutic Uses of Curcumin in Health and Disease, Adv. Exp. Med. Biol., vol. 595, Springer, Boston, MA., 471-472, 2 pgs. Apr. 2007.
"Cinnamon", World Encyclopedia of Medicinal Plants, Oct. 2000, p. 80 (2 pgs.).
"Diagnosis and Management of Upper Gastrointestinal (esophageal/gastric) diseases: How to Handle Intractable Vomiting", Proceedings of the 11th Japan Clinical Veterinary Forum 2009, vol. 11-1, pp. 3-181 to 3-185, Sep. 2009.
Abascal, et al., "The Medicinal Uses of Cinnamon", Integrative Medicine, vol. 9, No. 1, Feb.-Mar. 2010, 6 pgs.
Gronlien, et al., "Importance of M2-M3 loop in governing properties of genistein at the α7 nicotinic acetylcholine receptor inferred from α7/5-HT3A chimera.", European Journal of Pharmacology, vol. 647, Issues 1-3, Nov. 25, 2010, pp. 37-47.
Lee, et al., "Resveratrol Enhances 5-Hydroxytryptamine Type 3A Receptor-Mediated Ion Currents: The Rol of Arginine 222 Residue in Pre-transmembrane Domain I", Biol. Pharm Bull. 34(4), 523-524, Apr. 2017.
Malloy, "The Use of Vitamin B Complex and Vitamin C for the Postoperative Patient", Journal of the National Medical Association, May 1950, 7 pages.
McGrotty, "Medical Management of Acute and Chronic Vomiting in Dogs and Cats", Companion Animal Practice, in Practice, Nov./Dec. 2010, 6 pages.
Oliveira Leite, et al., "Attenuation of visceral nociception by α-bisabolol in mice: investigation of mechanisms", Organic and Medicinal Chemistry Letters. 2012; 2:18, Published online May 21, 2012, 5 pgs.
Wang, et al., "Antiemetic Effect of the Combination Treatment of Extracts of Capsicum and Gingers", Herald of Medicine, vol. 127, No. 13 Mar. 2008, Abstract, 4 pages.
Yang, et al., "Structure-antiemetic-activity of some Diarylheptanoids and their Analogues", Phytomedicine, vol. 9, pp. 146-152, 2002 (available online Nov. 2004).
Youn, et al., "Regulation of the 5-HT3A Receptor-Mediated Current by Alkyl 4-Hydrroxybenzoates isolated from the Seeds of Nelumbo nucifera", Chemistry and Biodiversity, vol. 7, Nov. 2010, 7 pgs.
Yu, et al., "Luteolin, a non-selective competitive inhibitor of phosphodiesterases 1-5, displaced [3H]-rolipram from high-affinity rolipram binding sites and reversed xylazine/ketamine-induced anesthesia", European Journal of Pharmacology, vol. 627, Issues 1-3, Feb. 10, 2010, pp. 269-275.
Zhao, et al., "Clinical experience of Chinese medicine rhubarb in treating vomiting", Journal of Jiamusi Medical College, vol. 16, No. 3, Mar. 16, 1993 (machine trans), 3 pages.
"All Natural Petcare", http://allnaturalpetcare.com/blog/2012/03/21/easy-natural-essential-oil-recipe-dog-nausea-vomiting (Mar. 2012), 7 pgs.
"Ginger Oleoresin", http://www.essentialoil.in/ginger-oleoresin.html?s1=en (Feb. 2018), 4 pgs.
"Pet Remedy Charts", http://petremedycharts.blogspot.com/2011/06/how-to-make-ginger-tea-for-nausea.html (Jun. 2011), 3 pgs.
Bishnoi, et al., "Protective effect of curcumin and its combination with piperine (bioavailability enhancer) against haloperidol-associated neurotoxicity: cellular and neurochemical evidence", Neurotox Res. 2011; 20:215-225.
Boles, et al., "Treatment of cyclic vomiting syndrome with co-enzyme Q10 and amitriptyline, a retrospective study", BMC Neurol., 2010, 10:10, 5 pages.
Khojasteh, et al., "Casopitant: a new warrior in the antiemetic crusade", Expert Opin Pharmacother. Jun. 2, 2009;10 (8):1367-1376.
Hongxin, et al., "Anti-emetic effects of Lianqiao (Forsythia) on a emetic model in mink", Chinese Medicine Pharmacology and Clinical, Jun. 15, 2011: 27(3), pp. 74-76, certified translation.
Huang, et al., "Application of Shengjiang Powder in Diabetic Gastroparesis", Journal of Sichuan of Traditional Chinese Medicine, vol. 121, No. 12, pp. 91-92, Dec. 2003.

* cited by examiner

DIETARY COMPOSITION AND METHOD FOR PREVENTING, REDUCING, ALLEVIATING OR TREATING IDIOPATHIC VOMITING

FIELD OF THE INVENTION

This invention is related to a dietary composition or a method for preventing, reducing, alleviating, or treating idiopathic vomiting in mammals, particularly domestic cats, using one or more plant materials or extracts that have inhibitory effect against the 5-hydroxytryptamine-3 serotonin (5-HT3a) and/or the neurokinin-1 (NK-1) receptor.

BACKGROUND OF THE INVENTION

Chronic/cyclic idiopathic emesis or vomiting syndrome in cats was identified in the late nineteenth century. Although infrequent vomiting by cats under certain circumstances may be acceptable, e.g., eating too fast or too much or presence of excessive hair or other foreign objects in the stomach, frequent vomiting or regurgitation without causes ("idiopathic vomiting") can result in severe malnutrition in cats and cause damages to the gastrointestinal (GI) health of the cats. The four main characteristics that define idiopathic vomiting are: 1) three or more recurrent separated episodes of vomiting or regurgitation; 2) varying intervals of completely normal, healthy periods between the episodes; 3) episodes are typical with regard to the timing of onset, symptoms and durations; and 4) unknown causes of vomiting or regurgitation. Subjects susceptible to idiopathic vomiting cannot be identified by standard medical examination, including physical examination and/or blood work. In humans, idiopathic vomiting may be described as Cyclic Vomiting Syndrome (CVS), and may be associated with dehydration, injury to the GI tract (particularly the esophagus), and tooth decay (vomitus may be acidic).

The exact causes of idiopathic vomiting are not fully understood. However, it has recently been recognized that one of the potential causes in cats is related to central nervous system (CNS) disorders. There are several neurotransmitter receptors in the brain of the cats that can be triggered to stimulate or activate different biological pathways leading to emesis. Examples of such receptors include neurokinin (NK) receptors, histamine receptors, acetylcholine receptors, serotonin receptors, mu-opioid receptors, and dopamine-2 receptors. Therefore, a potential way to prevent or reduce idiopathic vomiting is to inhibit or partially block such receptors.

Certain 5-HT3a receptor antagonists, such as dolasetron, granisetron, ondansetron, and palonosetron, have demonstrated effectiveness as an antiemetics in humans and have been used to manage chemotherapy-induced nausea and vomiting in cancer patients. Further, a new class of drugs known as NK-1 receptor antagonists has been recently developed for controlling emesis in humans, which include aprepitant and maropitant, among others. However, these compounds often lead to side effects. Further, it is difficult to administer such compounds through feeding, because of their undesirable taste. Unfortunately, injection is not a convenient alternative means of administering antiemetics. When treating animals, such as cats or dogs, injection may require veterinary assistance, particularly if the animal resists the injection.

Therefore, there is a continuing need for an effective and more readily available treatment for preventing, reducing, alleviating, or treating idiopathic vomiting. There is also a need for treatments with lesser side effects that can be easily administered such as, for example, through feeding or other oral administration. There is still further a need for naturally-derived therapeutic compounds or compositions. These needs are particularly acute for domestic cats with a history of idiopathic vomiting.

SUMMARY OF THE INVENTION

One aspect of the present invention meets the above-described needs by providing a dietary composition for preventing, reducing, alleviating, or treating idiopathic vomiting in a companion animal, which contains one or more plant materials or extracts thereof in an effective amount for inhibiting a 5-hydroxytryptamine-3a serotonin (5-HT3a) receptor and/or the neurokinin-1 (NK-1) receptor.

In another aspect, the present invention relates to a method for preventing, reducing, alleviating, or treating idiopathic vomiting in a companion animal, which includes the step of orally administering to said companion animal one or more plant materials or extracts thereof in an effective amount for inhibiting the 5-HT3a receptor and/or the NK-1 receptor.

In a further aspect, the present invention relates to a composition for preventing, reducing, alleviating, or treating idiopathic vomiting in a companion animal, which contains one or more plant materials or extracts thereof in an effective amount for inhibiting the 5-HT3a receptor and/or the NK-1 receptor.

In a still further aspect, the present invention relates to a package for preventing, reducing, alleviating, or treating idiopathic vomiting in a companion animal, comprising:

(a) a dietary composition; and
(b) a feeding manual providing written instructions for an owner of said animal.

Specifically, the feeding manual may include information on: (1) optionally, method of assessing severity of the idiopathic vomiting condition of the companion animal; (2) frequency of feeding; (3) duration of feeding; (4) method of feeding; and (5) optionally, method of monitoring the idiopathic vomiting condition of the companion animal to determine when to stop the feeding.

These and other aspects of the present invention will become more apparent upon reading the following detailed description and examples of the invention.

DETAILED DESCRIPTION OF THE INVENTION

Figure 1:
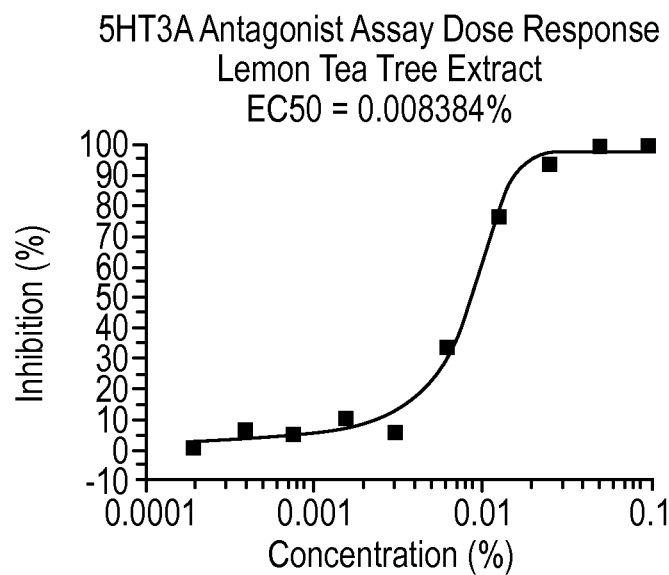
FIGS. 1 to 39 show the 5-HT3a dosage response curves of plant materials and extracts of the present invention with surprisingly high 5-HT3a inhibitory effect.

This application claims the benefit of U.S. Provisional Application Ser. No. 61/786,465, filed Mar. 15, 2013, the entirety of which is incorporated by reference herein.

Except as otherwise noted, the articles "a", "an", and "the" mean "one or more." The term "comprising" means that other steps and other ingredients which do not affect the end result can be added, and this term encompasses the terms "consisting of" and "consisting essentially of." The compositions and methods/processes of the present invention can comprise, consist of, and consist essentially of the essential elements and limitations of the invention described herein, as well as any of the additional or optional ingredients, components, steps, or limitations described herein. All percentages, parts and ratios are based upon the total weight of the compositions of the present invention, unless otherwise specified. All such weights as they pertain to listed ingredients are based on the active level and, therefore do not include carriers or by-products that may be included in commercially available materials. All ratios are weight ratios unless specifically stated otherwise. All temperatures are in Celsius degrees, unless specifically stated otherwise. All dimensions and values disclosed herein (e.g., quantities, percentages, portions, and proportions) are not to be understood as being strictly limited to the exact numerical values recited. Instead, unless otherwise specified, each such dimension or value is intended to mean both the recited value and a functionally equivalent range surrounding that value. For example, a dimension disclosed as "40 mm" is intended to mean "about 40 mm."

Herein, the term "treat," "treating" or "treatment" covers all manners of treatment of a disease or condition in the animal of interest, which includes: (i) inhibiting the disease or condition, i.e., completely arresting its development; (ii) reducing the disease or condition, i.e., causing regression of the disease or condition; and (iii) alleviating or relieving the symptoms resulting from the disease or condition, i.e., relieving pain or suffering without addressing the underlying disease or condition.

The term "effective" means an amount of a subject active high enough to provide a significantly positive modification of the condition to be treated. An effective amount of the subject active will vary with the particular condition being treated, the severity of the condition, the duration of the treatment, the nature of concurrent treatment, and like factors.

The term "vomit" or "vomiting" as used herein cover any voluntary or involuntary expulsion of contents from either one's stomach or esophagus into the mouth and sometimes into the nose. Such acts can be referred to variously as vomiting, regurgitation, emesis, throwing up, puking, heaving, and the like, but are collectively covered herein by the same term "vomit" or "vomiting."

The term "feline companion animal" or "feline" as used herein broadly covers all animals in the Felidea family that can potentially be taken in by humans as either indoor or outdoor companions, which include, but are not limited to: domestic cats, cougars, cheetahs, lynxes, ocelots, tigers, lions, jaguars, panthers, leopards, and the like. The term "companion animal" as used herein includes, but is not limited to: feline companion animals as described hereinabove; all animals in the Canidea family that can potentially be taken in by humans as either indoor or outdoor companions, such as domesticated dogs (*Canis familiaris*), wolves, foxes, jackals, coyotes, and the like; other smaller domestic mammals, such as ferrets, raccoons, rabbits, mice, rats, hamsters, guinea pigs, and the like.

The present invention has identified a specific group of plant materials or extracts thereof that are particularly effective as inhibitors of 5-HT3a and/or NK-1 receptor in felines and canines. Such plant materials or extracts are naturally derived with little or no side effects on the companion animals. Further, such plant materials or extracts have improved tastes or smells in comparison with synthetic compounds. Therefore, these plant materials or extracts can be readily used to formulate dietary compositions or regiments for managing and treating idiopathic vomiting in canines and felines. These plant materials or extracts may also be used in managing or treating idiopathic vomiting in other companion animals, or in other mammals, including in humans.

As used herein, the term "effective as inhibitors of 5-HT3a and/or NK-1 receptor" means a 5-HT3a and/or NK-1 receptor affinity ($IC_{50}$) of less than 100 ppm, preferably less than 50 ppm, and more preferably less than 10 ppm. To determine the 5-HT3a and/or NK-1 receptor affinity, various receptor binding assays well known in the art may readily be used.

Botanicals with 5-Ht3a Receptor Inhibitory Effect

It has been discovered by the inventors of the present invention that the following plant materials or extracts thereof have surprisingly high 5-HT3a receptor inhibitory effect with little or no cell toxicity:

*Leptospermum Scoparium* (lemon tea tree) leaf extract;
a water-soluble fraction of *Melaleuca alternifolia* (tea tree) oil;
*Rheum palmatum* (rhubarb);
*Lavandula angustifolia* (lavender tea tree) extract;
*Fusanus Spicatus* (Australian sandalwood) extract;
*Santalum Album* (sandalwood) oil;
*Evodia Rutaecarpa* (evodia) fruit;
*Coptis chinensis* (coptis) rhizome;
oils from *Wisteria sinensis;*
*Myrtus Communis* (myrtle) extract;
*Prunus serotina* (wild cherry) bark;
*Aquilaria sinensis* (Chinese Agarwood) resinous heartwood extract;
*Zingiber officinale* (ginger) root;
*Calendula officinalis* (marigold);
*Boswellia serrata* (boswellia);
oil from *Boswellia carterii* (frankincense oil);
*Zanthoxylum americanum* (prickly ash fruit) extract;
*Pinus pinaster* bark extract;
*Marrubium vulgare* (horehound);
*Citrus aurantium* (bitter orange) fruit;
*Angelica archangelica* (angelica);
*Cocos nucifera* (coconut) oil;
*Rosa chinensis* (Chinese rose);
*Cinnamomum aromaticum* (cinnamon);
*Vaccinium myrtillus* (bilberry) extract;
*Vaccinium corymbosum* (blueberry) leaf extract;
*Daucus carota* (carrot) extract;
*Anthemis eecutita* (chamomile) extract;
*Curcuma longa* (turmeric) extract;
*Vaccinium macrocarpon* (cranberry) extract;
*Linum usitatissimum* (flax) oil powder;
*Hovenia dulcis* (Japanese raisin tree) seed extract;
*Andrographis paniculata* (Andrographis herb) extract;
Bee pollen extract;
*Eucalyptus radiata* (Australia eucalyptus) extract;
Yerba santa extract;
*Piper nigrum* (black pepper) oil;
*Ginkgo biloba* extract; and
*Capsicum annuum* (cayenne) extract.

Further, it has been discovered that the following combinations of plant materials or extracts act in synergy as inhibitors of 5-HT3a receptor:

*Curcuma longa* (turmeric) and *Glycyrrhiza glabra* (licorice);
Turmeric, licorice, and ginger;
Turmeric and ginger;
Turmeric and rhubarb; and
Licorice, ginger, and rhubarb.

Botanicals with Nk-1 Receptor Inhibitory Effect

It has been discovered by the inventors of the present invention that the following plant materials or extracts thereof have surprisingly high NK-1 receptor inhibitory effect with little or no cell toxicity:

*Podophyllum peltatum* (podophyllin);
*Rhodiola rosea* (rhodiola);
*Tanacetum parthenium* (feverfew);
*Pinus massoniana* (pink bark);
*Boswellia serrata* (boswellia);
*Dracaena cinnabari* (Dragon's Blood) extract
*Tilia vulgaris* (linden);
*Paullinia cupana* (guarana);
*Uncaria tomemtosa* (cat's claw);
*Hypericum perforatum* (St. John's wort);
*Calendula officinalis* (calendula);
*Camellia sinensis* (green tea) extract;
*Vitis vinifera* (grape) extract;
*Cinnamomum aromaticum* (cinnamon) extract;
*Curcuma longa* (turmeric) extract;
*Fructus forsythiae* (forysthia fruit) extract;
*Glycyrrhiza glabra* (licorice) extract;
*Litsea cubeba* oil;
*Melaleuca alternifolia* (tea tree) oil; and
*Phyllanthus emblica* (amla) extract.

Further, it has been discovered that the combination of turmeric and licorice acts in synergy as inhibitors of NK-1 receptor.

Methods of Administration

The above-listed plant materials or extracts can be administered by any well-known delivery method, which includes, but is not limited to: oral delivery, inhalation, rectal injection, or parenteral delivery, such as, for example, topical application, transdermal application, intravenous injection, subcutaneous injection, intra-muscular injection, and the like. Such plant materials or extracts can be administered alone or in combination with any acceptable carriers or diluents to form compositions such as dry kibbles, wet canned food, gravies, treats, tablets, capsules, lozenges, troches, hard candies, powders, sprays, creams, salves, suppositories, jellies, gels, pastes, lotions, ointments, aqueous suspensions, injectable solutions, elixirs, syrups, and the like.

In a preferred but not necessary embodiment of the present invention, such plant materials or extracts are orally administered to a companion animal, for example, as a part of a dietary composition for the companion animal. Such a dietary composition can be a liquid, a solid, or a semi-solid. Further, the dietary composition may be formulated as either a pet food that is fed to the animal at meal times, or a pet food supplement that is fed to the animal either separately from or in combination with the pet food for the animal.

As a pet food, the dietary composition may comprise a nutritionally complete diet for the intended recipient companion animal. A nutritionally complete diet contains known required nutrients to sustain life of the companion animal in proper amounts and proportions based on recommendations of well recognized authorities, including governmental agencies such as United States Food and Drug Administration's Center for Veterinarian Medicine, the American Feed Control Officials Incorporated, with the exception of water.

For example, a pet food composition of the present invention may comprise at least a source of carbohydrate, a source of protein, and optionally a source of fat. More preferably, the pet food composition provides the companion animal with a nutritionally complete and balanced diet, which may comprise: from about 1% to about 99%, preferably from about 1% to about 90% and more preferably from about 5% to about 45%, by weight of carbohydrates; from about 5% to about 99.9%, preferably from about 10% to about 90% and more preferably from about 20% to about 60%, by weight of protein; from about 0.1% to about 50%, preferably from about 1% to about 40% and more preferably from about 5% to about 20%, by weight of fat; from about 0.01% to about 20%, preferably from about 1% to about 11%, by weight of dietary fiber; from about 0.01% to about 15%, preferably from about 0.1% to about 10% and more preferably from 1% to 8%, by weight of vitamins, minerals, antioxidants, and other nutrients supporting the needs of the companion animal. The carbohydrates can be provided by grains such as rice, corn, milo, sorghum, barley, wheat, oats and the like. The protein can be provided by either animal-derived sources, such as meats (beef, pork, lamb, poultry, fish, and the like), eggs, and milk, or plant-derived sources, such as soybean, cereals, cottonseed, peanut, and the like. The dietary fibers can be provided by cellulose, hemicellulose, pectin, lignin, and gums. Further, the pet food composition of the present invention may contain various ingredients typically used in pet foods, such as fillers, flavors, binding agents, thickeners, stabilizers, emulsifiers, sweeteners, food-grade colorants, buffers, salts, and the like. Particularly preferred binding agents and/or thickeners are gelatin, cellulose ethers, starch, starch esters, starch ethers, and modified starches.

The pet food composition can be formulated as dry kibbles, wet canned foods, gravies, or treats. It may be fed to the companion animal on a daily basis, either at regular meal times (such as, for example, from once a time up to six times a day) or continuously throughout the day as needed (for example, through an automatic feeder or by simply providing an excessive amount). The composition may be fed ad libitum.

In certain embodiments, the pet food composition is a treat. Treats as used herein refer to pet food compositions that are given to the companion animal to entice the animal to eat during a non-meal time. Treats may also have nutritional value and have a food-like composition including one or more nutrients as described hereinabove, but are not in themselves a nutritionally complete diet.

The dietary composition of the present invention can also be provided as a pet food supplement, which is used with another feed, either concurrently or separately, to improve the nutritive balance or performance of the companion animal. Pet food supplements include, but are not limited to, any composition that is fed undiluted in addition to other feeds, thereby offering free choice with other parts of an animal's ration that are separately available, or is diluted and mixed with an animal's regular feed to produce a complete feed. The Association of American Feed Control Officials (AAFCO) provides guidelines, for example, that contain a discussion relating to supplements, which can be in various forms including powders, liquids, syrups, pills, encapsulated compositions, and the like. Further, the pet food supplement can be provided as a part of a toy for the companion animal, with partially or fully consumable components.

The dietary compositions as described above can be readily formed by mixing one or more above-listed plant materials or extracts capable of inhibiting the 5-HT3a and/or NK-1 receptor with one or more above-disclosed dietary nutrients suitable for a companion animal.

To determine an efficacious dosage, multiple complete cross-over studies can be performed with the plant materials or extracts in the companion animal to be treated at various doses. The optimal dose is selected based on the maximal ability to reduce or eliminate idiopathic vomiting in companion animals exhibiting perceivable symptoms of idiopathic vomiting. When administered to the companion animal in form of a pet food composition, the plant materials or extracts as described hereinabove are preferably administered in dosages ranging from 0.1 ppm to 75,000 ppm, preferably from 1 ppm to 1000 ppm. When administered in form of a supplement, the plant materials or extracts as described hereinabove are preferably administered in dosages ranging from 0.1% to 99%, preferably from 0.5% to 15%, by weight of the supplement. The composition is preferably a dietary composition, but can be any other composition, which includes, but is not limited to: topical compositions, injectable compositions, nasal compositions, rectal compositions, and the like.

Frequency and duration of the administration can be varied depending on the animal's condition, the species of animal being treated, its individual response to the treatment, and the type of pharmaceutical formulation chosen. Frequency can range from once a month to six times a day, preferably from once a week to four times a day, and more preferably from once a day to three times a day. Duration can range from five days to the entire life span of the animal, e.g., twenty five years. Preferably, the duration ranges from one week to fifteen years, more preferably from two weeks to one year, and most preferably from one month to six months.

Other kinds of vomiting or regurgitation may occur concurrently with idiopathic vomiting. Compositions of the present invention may include features to reduce other causes of vomiting. For example, a food composition may include large food particles relative to the size of the subject animal's mouth, to discourage rapid eating that may cause regurgitation; or may include ingredients to reduce the occurrence of hairballs, such as proteases, polyol fatty acid polyesters, laxatives, and the like; or may include ingredients to promote gastrointestinal health, such as prebiotics or probiotics. Compositions of the present invention may include medicinal drugs with anti-emetic activity.

Kit Containing the Dietary Composition

The present invention also covers an article of commerce, preferably in form of a kit, containing the dietary composition as described hereinabove together with instructions that provide information on how to orally administer or feed the dietary composition to the companion animal. Specifically, the instructions may provide information on, for example: assessing the severity of the idiopathic vomiting condition of the companion animal; frequency of feeding; duration of feeding; mode of feeding; and monitoring the idiopathic vomiting condition of the companion animal to determine when to modify the frequency and/or the duration of feeding.

Any standard packaging that is suitable for delivery and sale of the dietary compositions as disclosed herein can be used in forming the kit. The kit can also include specific written benefit statements related to the prevention, reduction, and elimination of idiopathic vomiting or emesis in companion animals. The benefit statements can also relate to the health benefits resulted from such prevention or treatment of idiopathic vomiting or emesis, such as increased body weight and energy level, improved immune functions, and prolonged life span.

The present invention is illustrated by the following examples. It will be understood, however, that the invention is not limited to the specific details of these examples.

EXAMPLES

Assays for Screening 5-Ht3a Receptor Inhibitors

Various known high through-put screening assays can be used to determine the inhibitory effects of a material on 5-HT3a receptors.

For example, the 5-HT3a receptor is a ligand-gated, non-selective cation channel located in the central and peripheral nervous system. Activation of the $5\text{-HT}_{3a}$ receptor followed by rapid depolarization of the peripheral or central neuron causes a rapid rise in cytosolic $Ca^{2+}$ and $Na^+$ concentration by inducing calcium and sodium influx and mobilization of intracellular calcium stores, as well as modulating the release of various neurotransmitters and neuropeptides such as dopamine, cholecystokinin, acetylcholine, GABA, substance P or serotonin itself. Due to activation of 5HT3 receptor following calcium and sodium influx and the subsequent rapid intracellular calcium and sodium increase, a calcium indicator (e.g., Fluo-4 AM) or a sodium dye can therefore be readily used to detect influx $Ca^{+2}$ or $Na^+$ signal using the Fluorometric Imaging Plate Reader (FLIPR) assay to identify agonists or antagonists of $5\text{-HT}_{3a}$ receptors.

The 5-HT3a FLIPR assay can specifically be conducted by the following steps. First, HEK-23 (human embryonic kidney) cells stably expressed with h5HT3A receptor are grown in 16-18 ml growth medium in a 75 $cm^2$ flask for 2-3 days at 37° C. in a mammalian cell culture incubator with 5% $CO_2$ and 90% humidity. The growth medium may contain, for example, DMEM/F12 (1:1, Invitrogen 11039) supplemented with 10% FBS (fetal bovine serum), 100 µg/ml Antibiotic/Antimycotic, and 150 ug/ml G418. The cell medium is then transferred to a 50 ml tube, and the cells are washed with 10 ml PBS. Subsequently, 2 ml of 0.05% Trypsin-EDTA is added to detach cells, and the above cell medium is added back to flask to inactivate trypsin. Next, the cells are transferred back to the above 50 ml tube, which is centrifuged at 850 rpm for 3 minutes to remove medium. The cells obtained from centrifugation are then re-suspended with growth medium at 1-1.5 ml per flask cells. One vial of Fluo-4 AM (calcium indicator, 50 ug) is subsequently dissolved with 20 ul of Pluronic F-127, and 10 ul of Fluo-4 AM solution per flask cells is added (1 vial of Fluo-4 AM solution, 20 ul, is good for 2 flask of cells). The cells are then stained with Fluo-4 AM for 30 min at room temperature with gently shaking on a shaker, followed by addition of 45 ml of the assay buffer [HBSS with $CaCl_2$ and $MgCl_2$ (Invitrogen 14025), 20 mM HEPES, pH7.2] to wash cells once. Centrifugation is carried out once more at 850 rpm for 3 minutes to remove assay buffer. The resulting cell pellet is again re-suspended in Assay buffer (per flask cells with 18-20 ml assay buffer). Ninety microliters of cells (50K cells/well) is loaded in the 96-well plates that are pre-loaded with the plant materials or extracts to be tested (10 ul of 1 mM test materials, the final concentration of the test materials will be 100 uM). The plates are placed at room temperature for 15-30 min in dark and then transferred to FLIPR-384 instrument (Molecular Devices). The master plate containing 6× of agonist (60 uM serotonin) is placed, and all test plates are read after adding agonist. The calcium signal of the test plates is finally recorded by the FLIPR program. The average and standard deviations are calculated using Excel, and the background (buffer) is subtracted. The percentage (%) inhibition is then calculated as $$\left(1 - \frac{\text{Test Material}}{\text{Agonist Control}}\right) \times 100.$$

A test material will be considered as having an inhibitory effect against the 5-$HT_{3a}$ receptor if the percentage inhibition calculated is greater than 40%.

Alternatively, a cell-based serotonin receptor assay can be used to screen inhibitors of the 5-HT3a receptor. Using the agonist serotonin and cells co-transfected to over express the 5-HT3a receptor and the luminescent aequorin calcium sensitive reporter, this assay can be conducted to identify suitable new actives targeting the 5-$HT_{3a}$ receptor with great sensitivity, scalability and specificity.

Aequorin is a photo-protein originating from the Jellyfish *Aequorea Victoria*. It is initially translated as an apo-enzyme requiring the hydrophobic group coelenterazine to initiate the conversion to aequorin. Upon binding of calcium, the coelenterazine is oxidized by aequorin into coelenteramide (BFP) resulting in the emission of blue light and $CO_2$. Therefore, it is particularly useful for visualizing or detecting influx $Ca^{+2}$ signal.

The aequorin-assisted serotonin receptor assay can be carried out with the following steps. Cyro-preserved Human Cells (HEK293 parent line), co-expressing Serotonin 5HT3a receptor and the Aequorin calcium sensor, γ-Irradiated (Perkin Elmer, Cat. No. ES-402-AF) are thawed and cultured 18-24 hours in DMEM/F12 with Hepes buffer, no phenol red+10% FBS without antibiotics (Invitrogen, Cat. No. 11039-021). After 18-24 h of culture, the cells are detached gently by flushing with their cell culture medium. Washing with an additional 10 mLs of cell culture media will ensure that optimum number of cells is captured. The cells are then centrifuged at 150×g, counted and re-suspended at 1×10^6 cells/mL in BSA medium [DMEM/Ham's F12 (with 15 mM HEPES, L-glutamine, without phenol red) culture medium (Invitrogen, Cat. No. 11039-021)+10% protease-free BSA (Sigma Aldrich, Cat. No. A9205) in $H_2O$ with a final BSA concentration of 0.1%] in a Falcon tube. Coelenterazine is added at a final concentration of 5 μM in assay medium. As coelenterazine stock solution is in methanol, it is mixed well while adding the coelenterazine solution to the cell suspension to avoid damaging the cells. The 10 mL Falcon tube is then wrapped in aluminum foil and placed on a rotating wheel (about 45° angle and 7 rpm). The cells are subsequently incubated from 4 hrs to 18 hrs at ~20° C. (temperature should remain below 25° C.). On the day of the assay, cells are diluted in BSA medium to a final concentration of 2.0×10^5 cells/mL. The cells are incubated again for at least 1 h at room temperature. The screen plates are then prepared. Antagonists are diluted in BSA medium referenced above at 2× concentration, and 50 μl are dispensed per well.

Fifty microliters of cell suspension (2.0×10^5/ml for a final concentration of 1.0×10^4/well) is added into the antagonist wells and then incubated for 15 minutes in the dark at room temperature. Only one plate is prepared at time. Fifty microliters of serotonin (3×EC80 (EC stands for Effective Concentration) concentration (30 μM) to get 1×EC80 (10 μM) final concentration) is injected using the plate readers injectors into the mix of cells and antagonist, and the light emitted is recorded for 10 s. An 8 point dose curve was conducted using the agonist serotonin to determine the EC50 for this system. Doses ranged from 3.9E-7 to 5E-5 [M]. The resulting EC50 was determined to be 1.925E-6±3.715E-6 [M].

Figure 2:
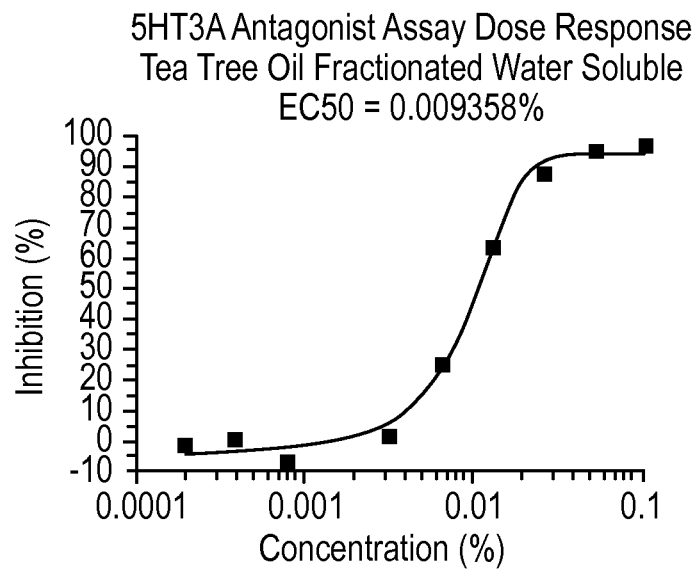
Figure 3:
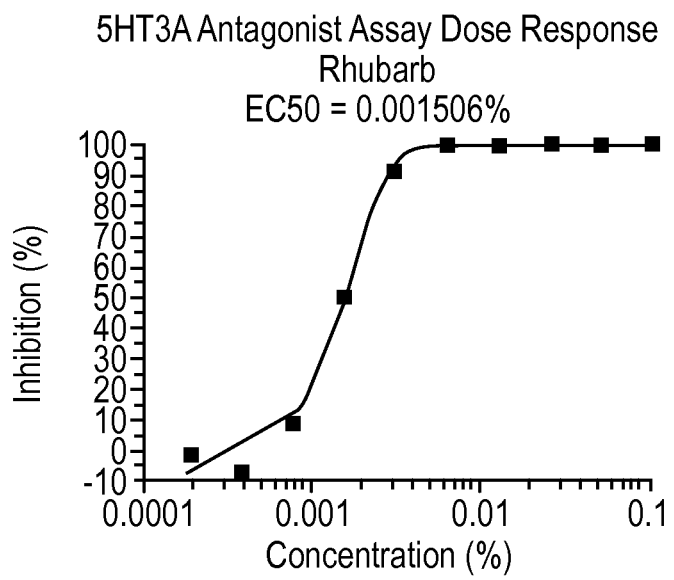
Figure 4:
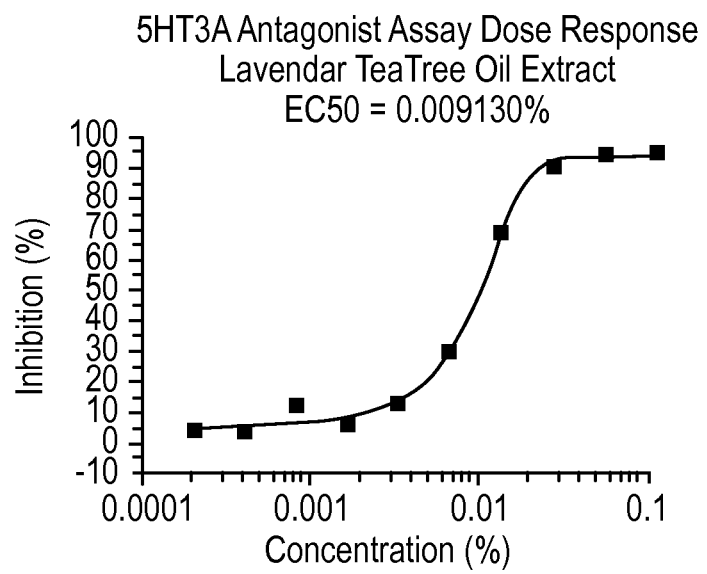
Figure 5:
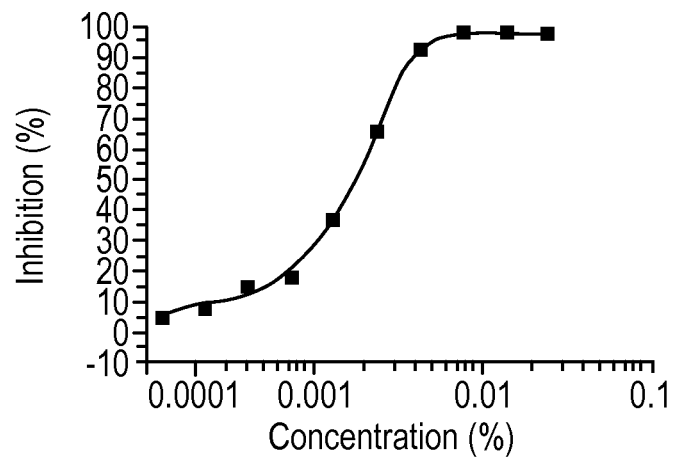
Figure 6:
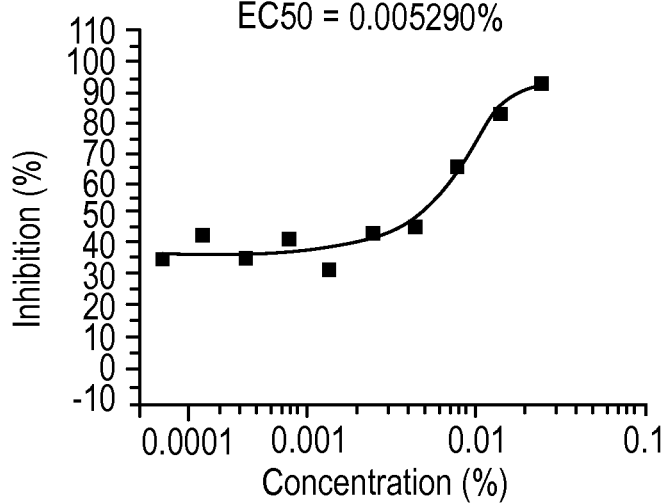
Figure 7:
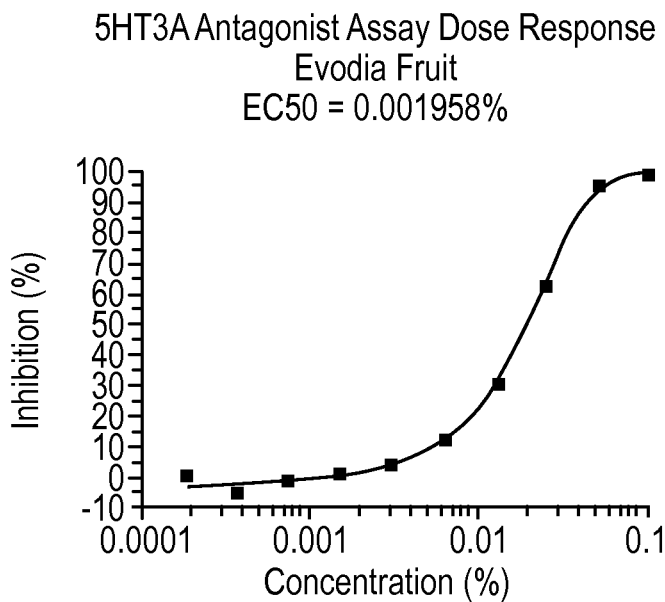
Figure 8:
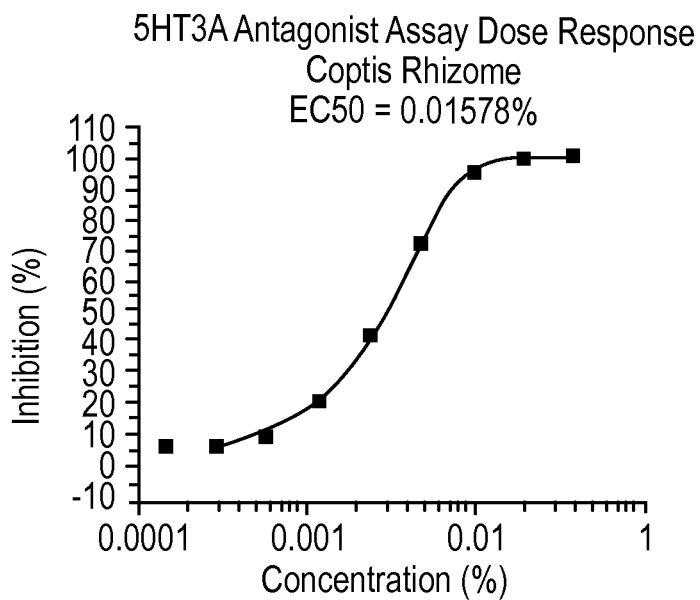
Figure 9:
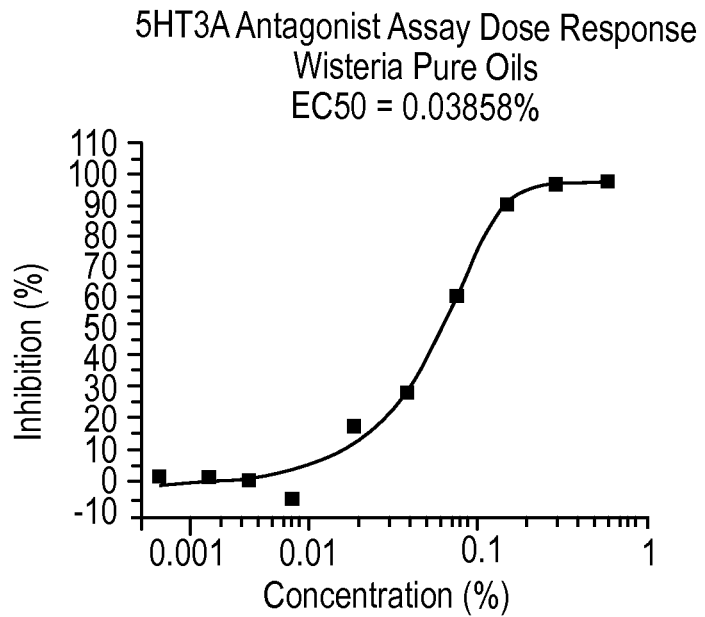
Figure 10:
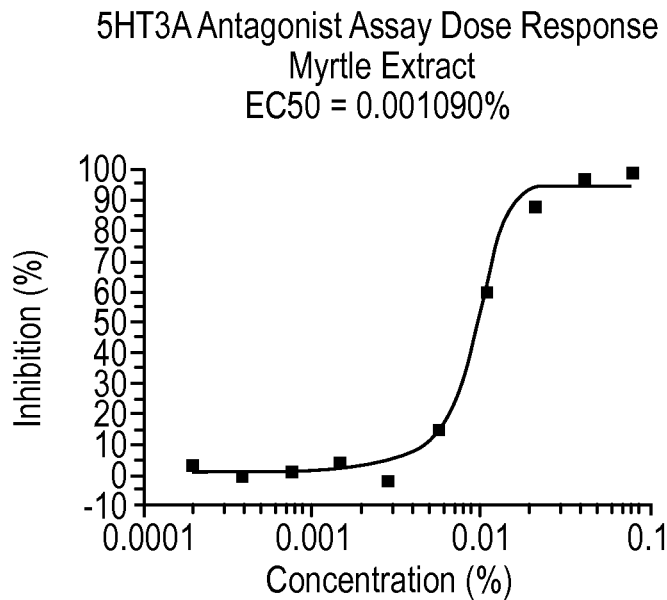
Figure 11:
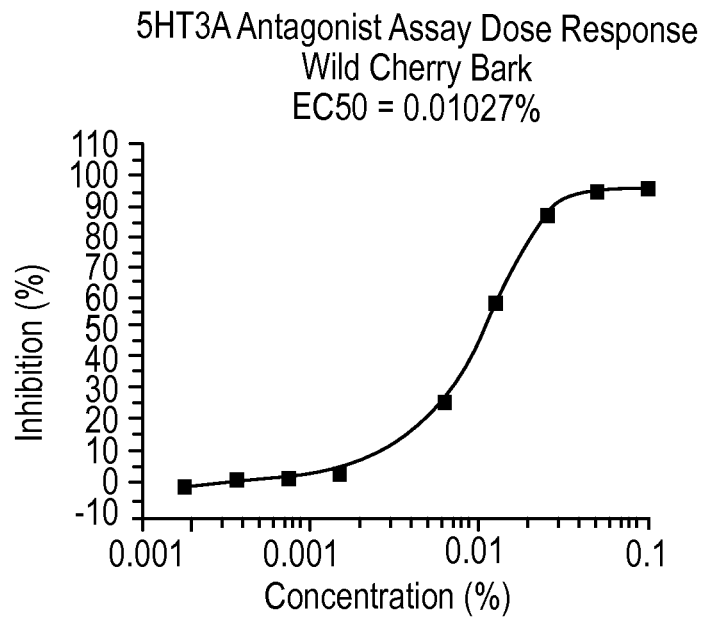
Figure 12:
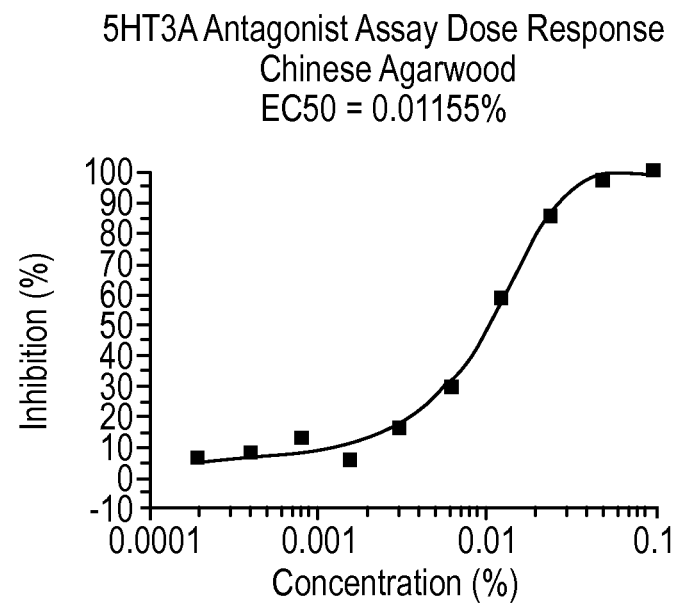
Figure 13:
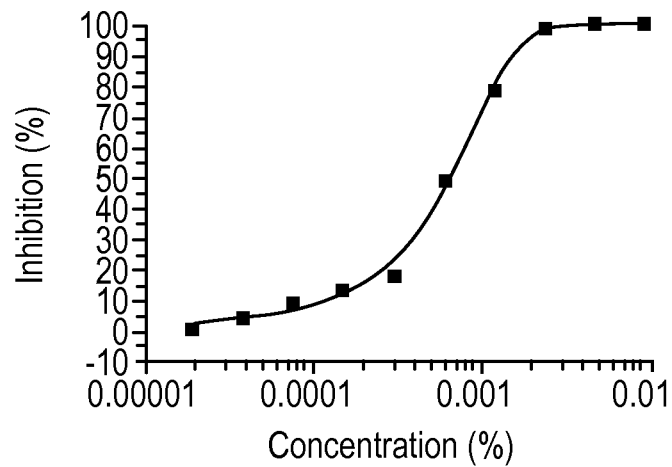
Figure 14:
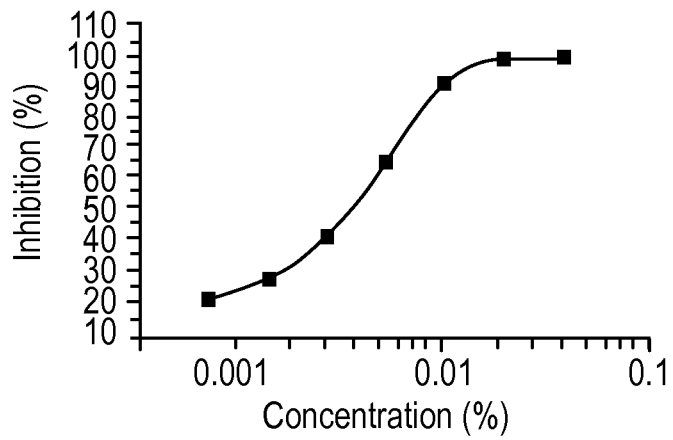
Figure 15:
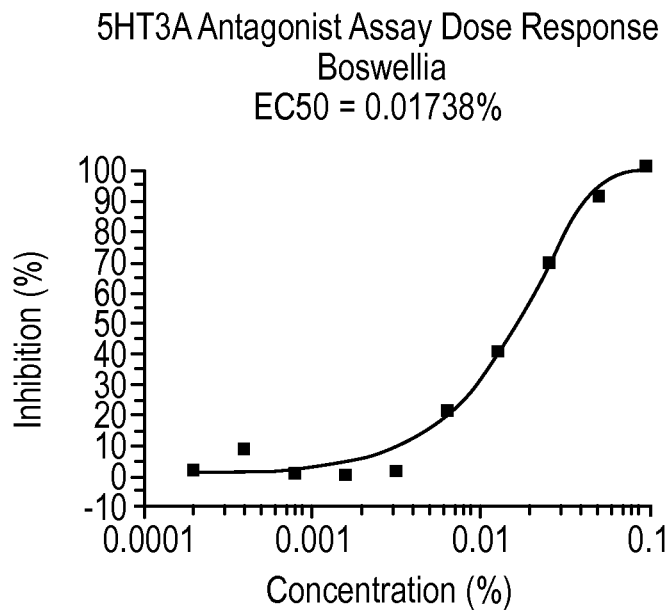
Figure 16:
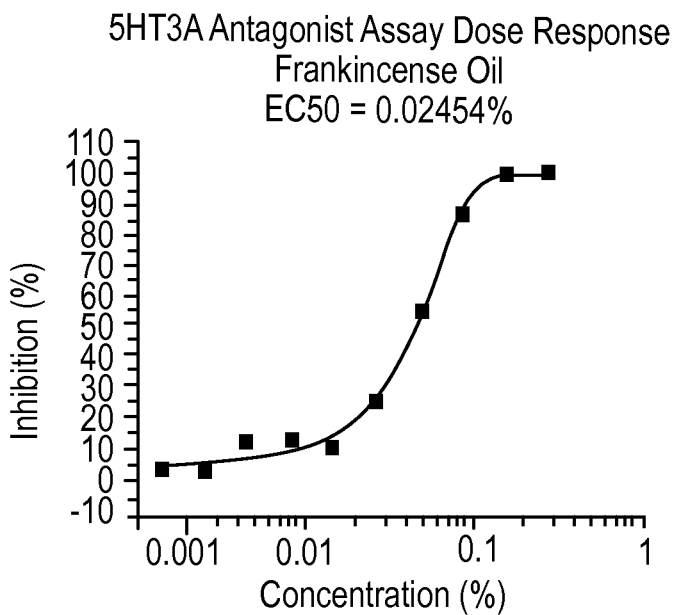
Figure 17:
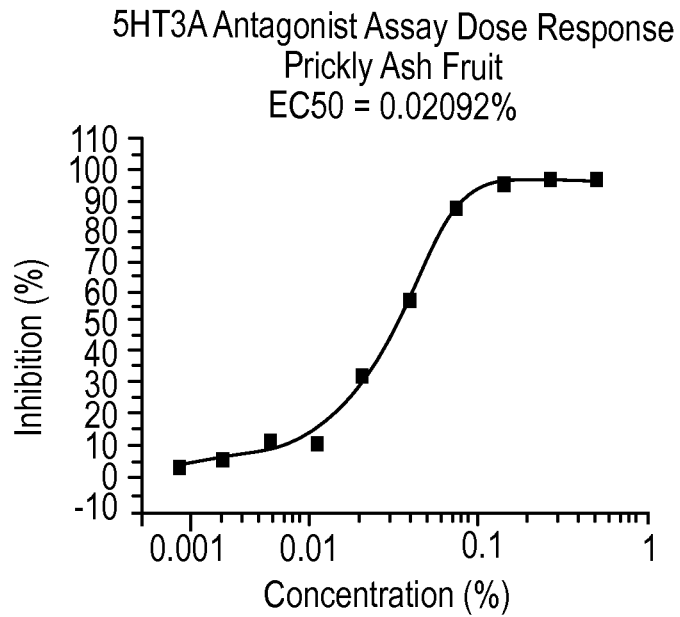
Figure 18:
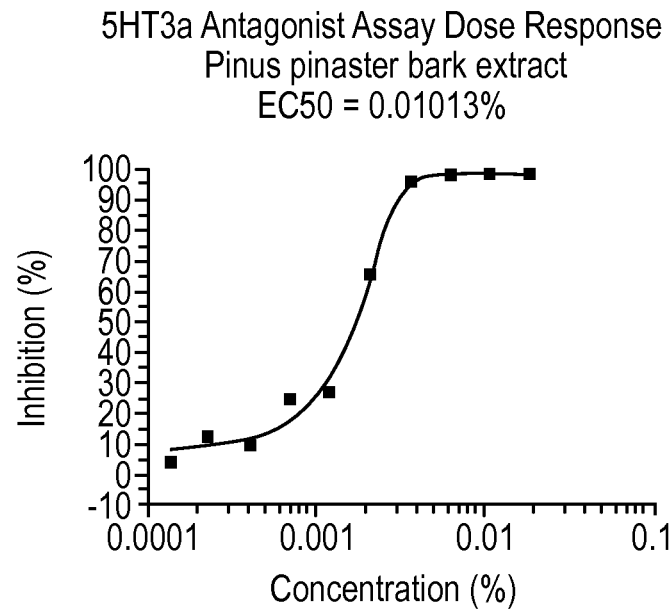
Figure 19:
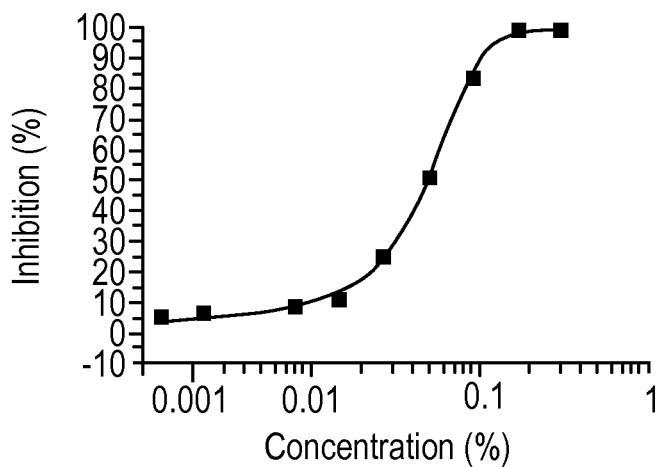
Figure 20:
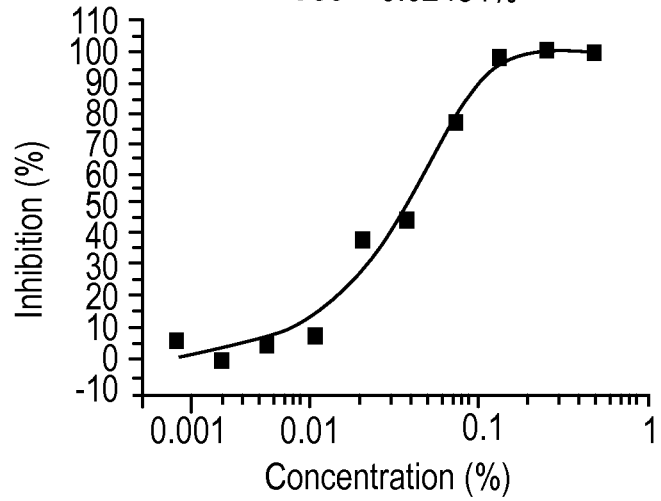
Figure 21:
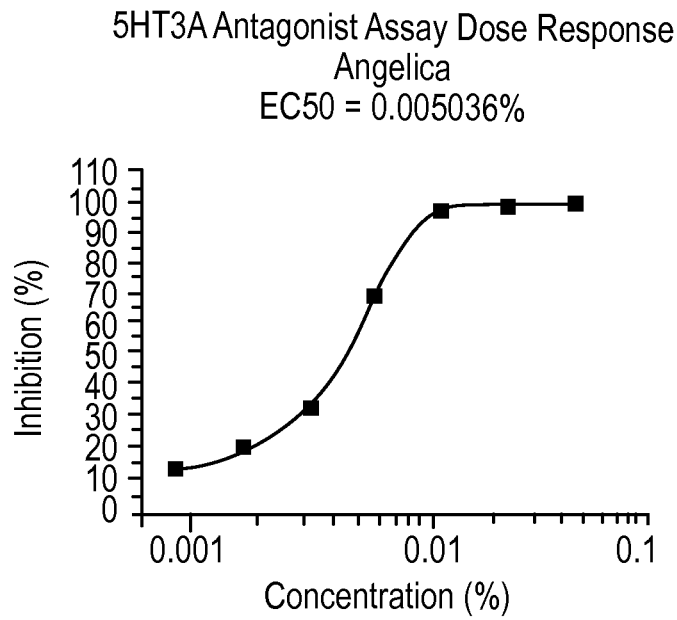
Figure 22:
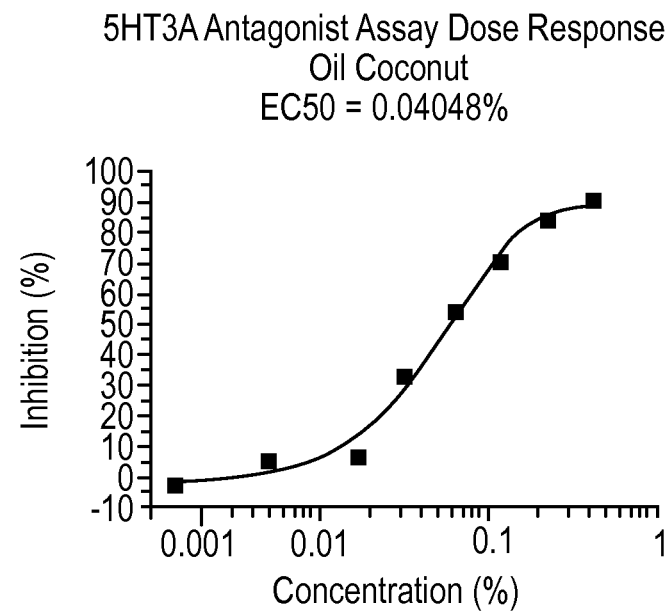
Figure 23:
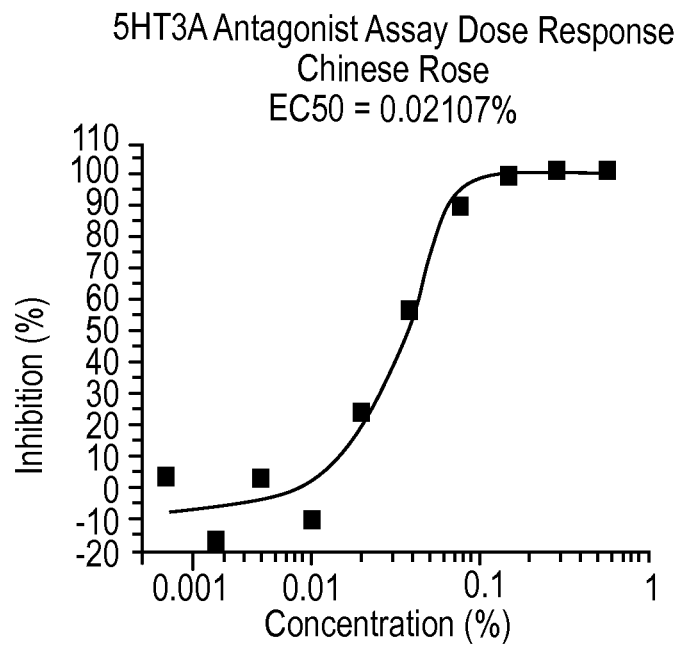
Figure 24:
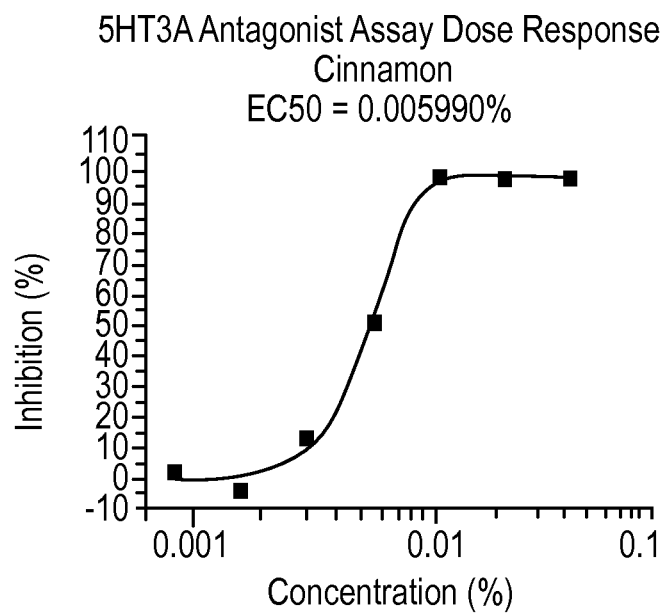
Figure 25:
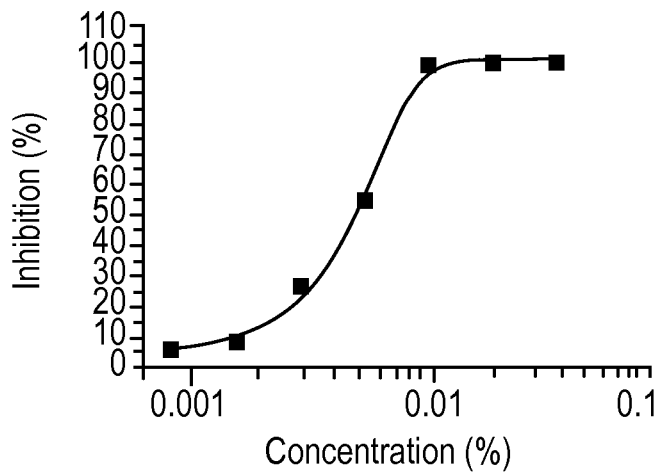
Figure 26:
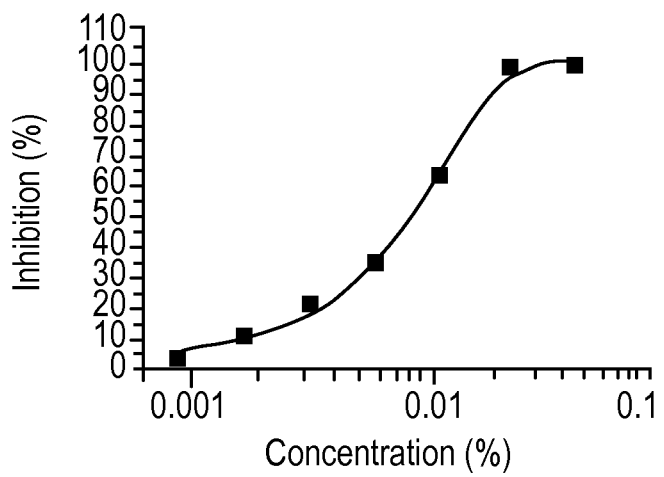
Figure 27:
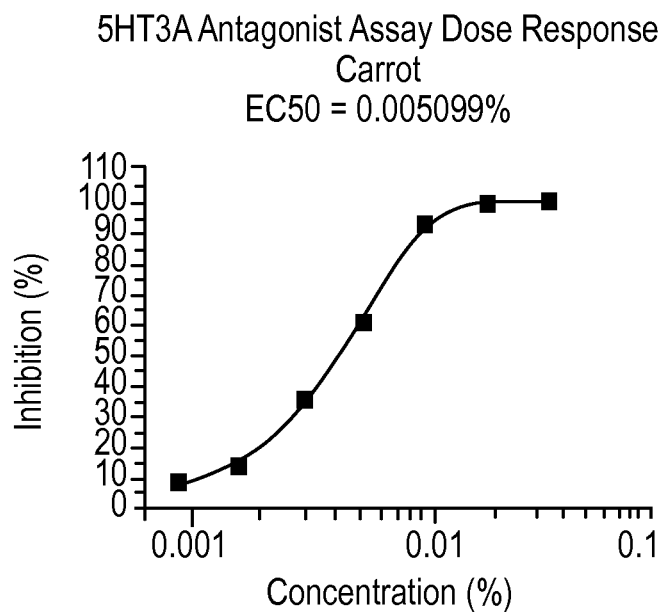
Figure 28:
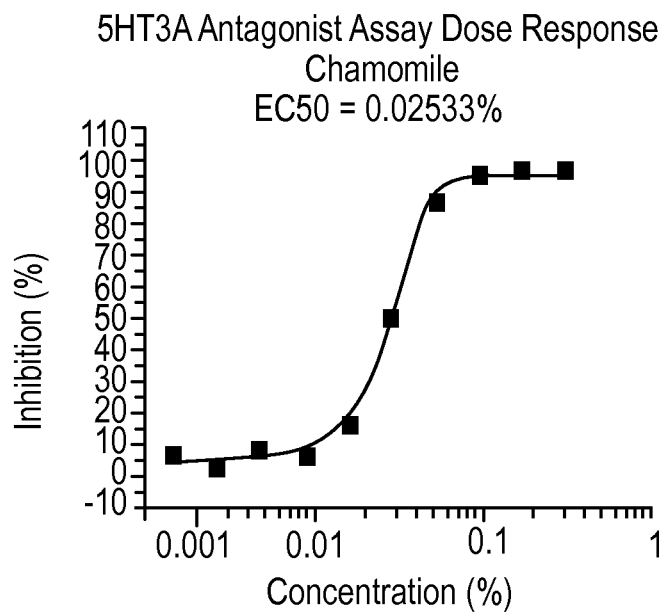
Figure 29:
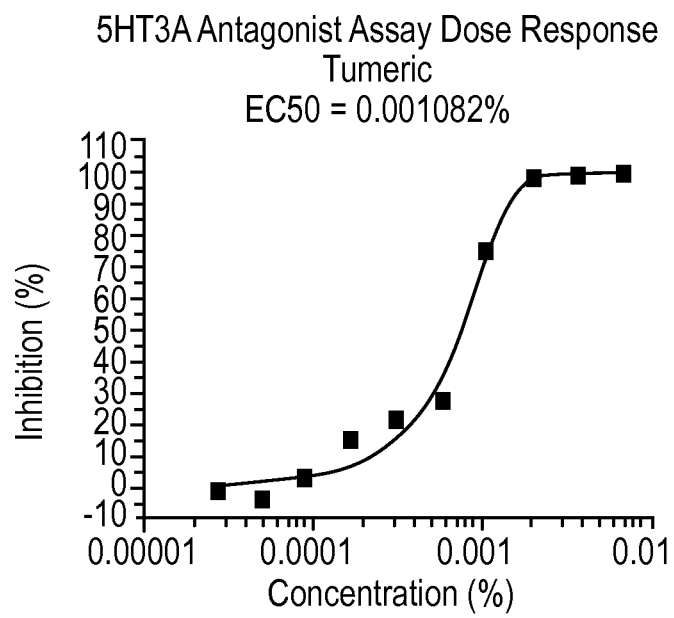
Figure 30:
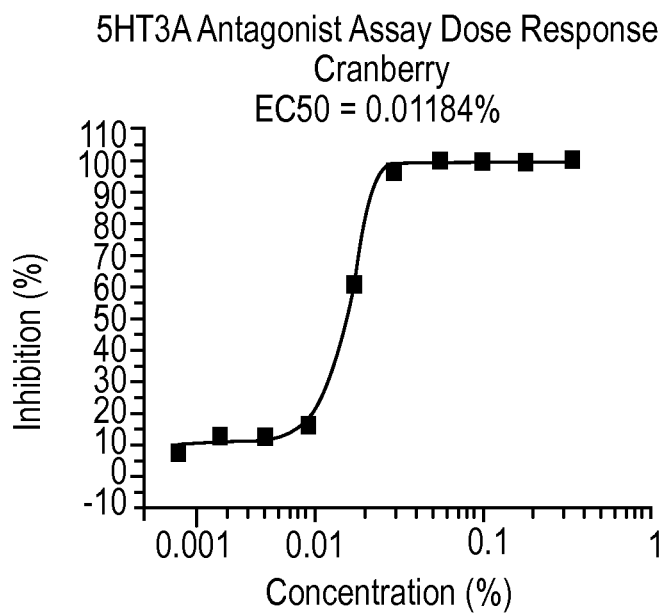
Figure 31:
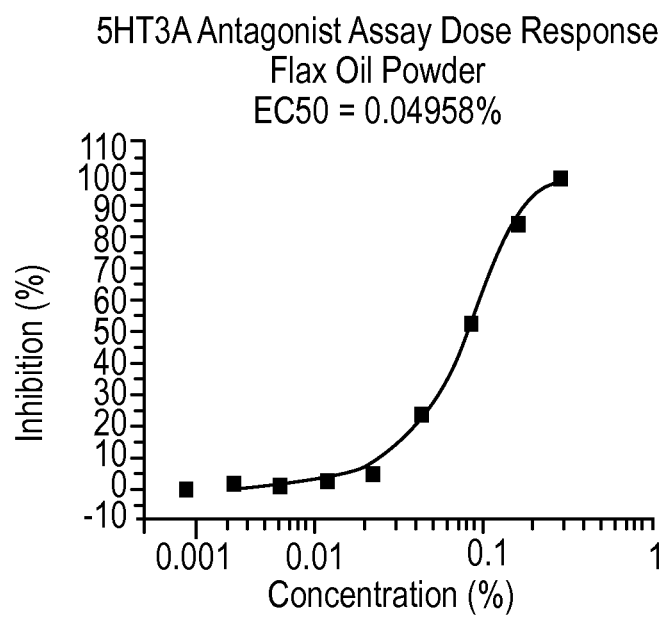
Figure 32:
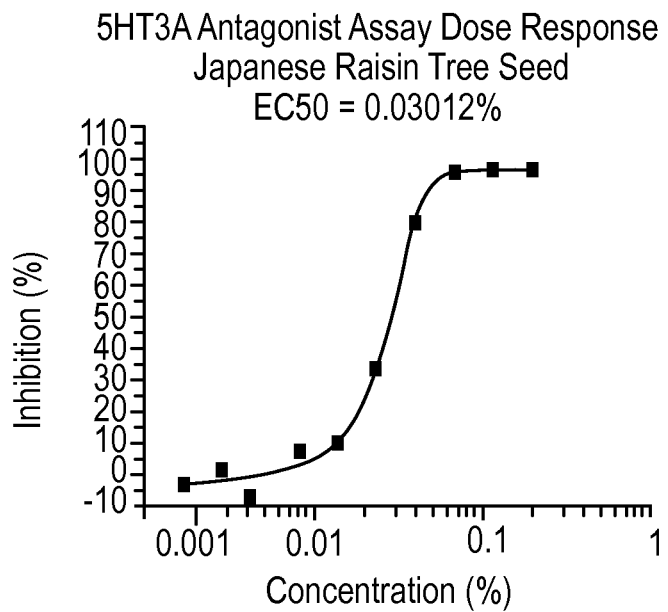
Figure 33:
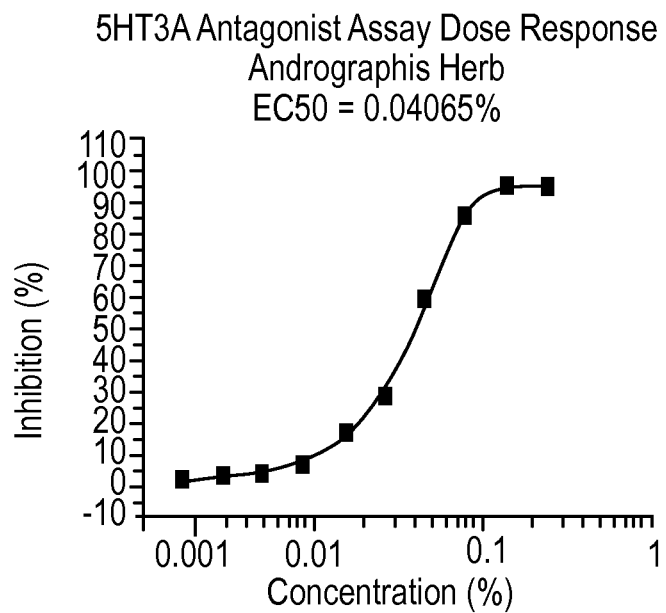
Figure 34:
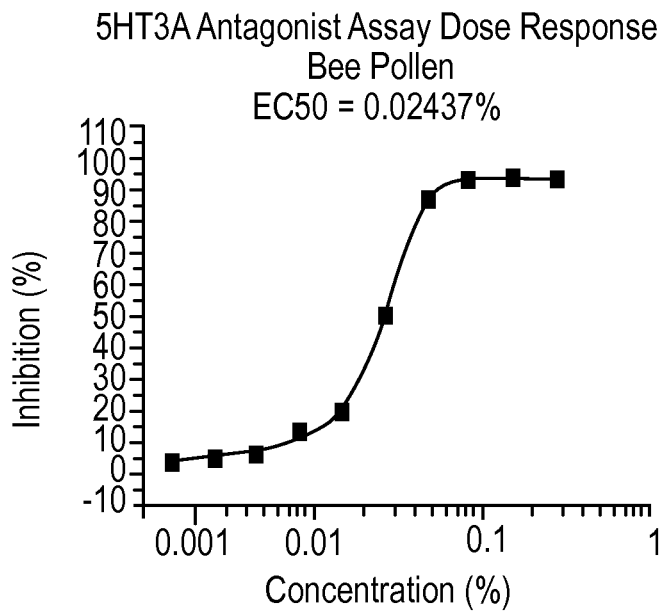
Figure 35:
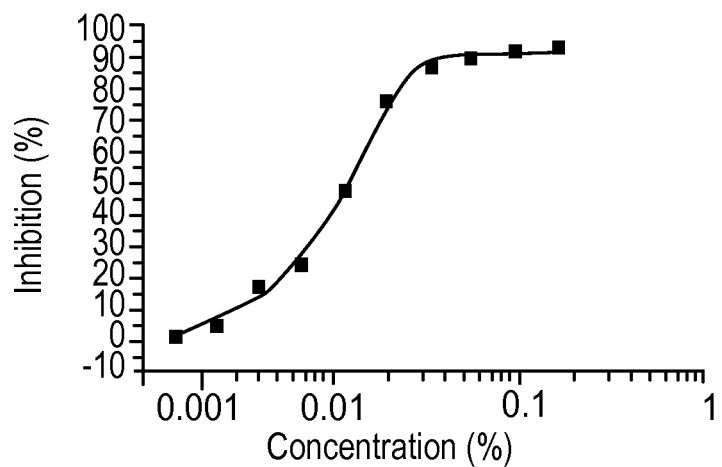
Figure 36:
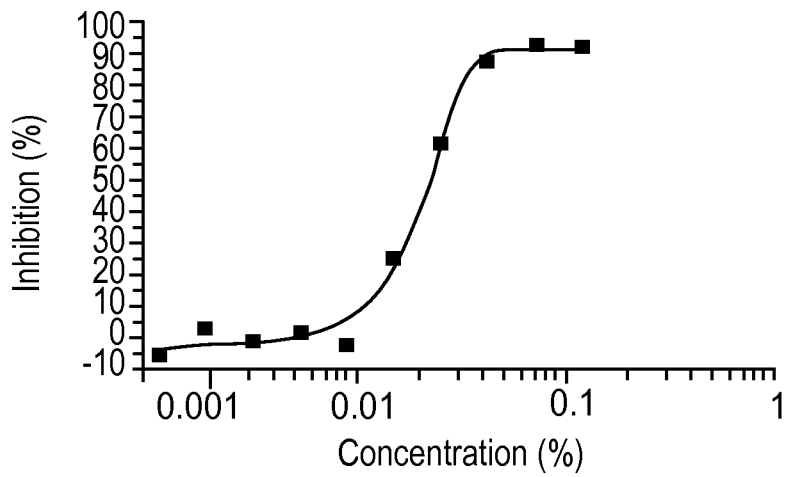
Figure 37:
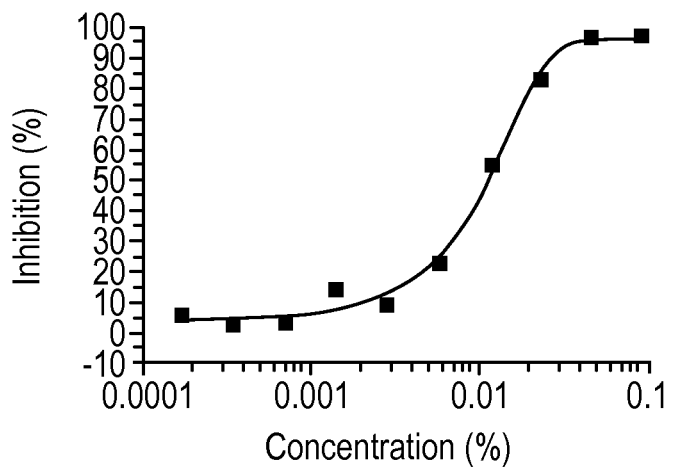
Figure 38:
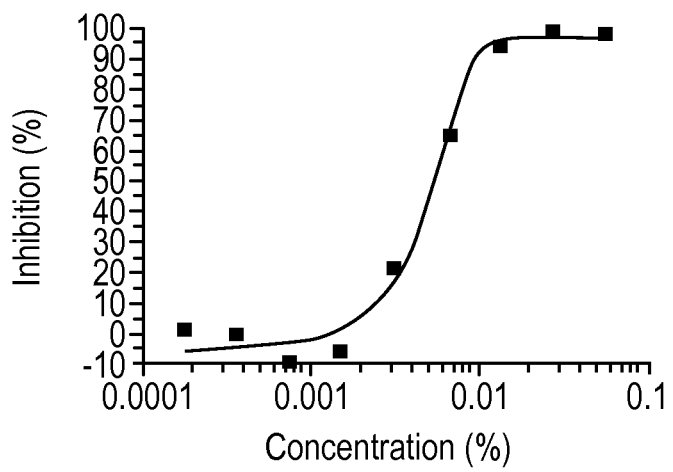
Figure 39:
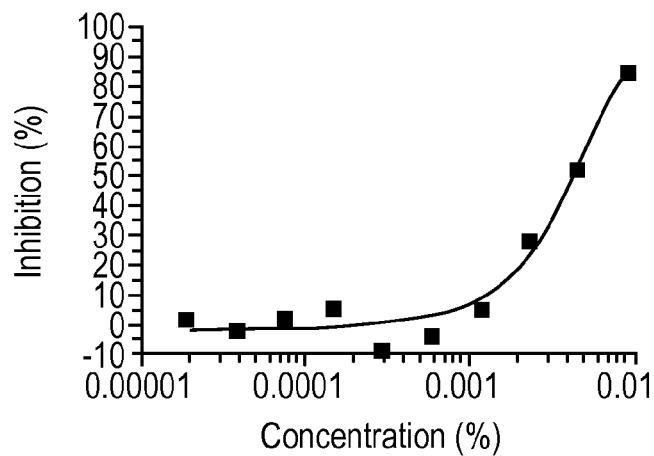

FIGS. 1 to 39 show the 5-HT3a dosage response curves of plant materials and extracts described hereinabove with high 5-HT3a inhibitory effect. Specifically, FIG. 1 shows the 5-HT3a dosage response curve of lemon tea tree leaf extract. FIG. 2 shows the 5-HT3a dosage response curve of a water-soluble fraction of tea tree oil. FIG. 3 shows the 5-HT3a dosage response curve of rhubarb. FIG. 4 shows the 5-HT3a dosage response curve of lavender tea tree extract. FIG. 5 shows the 5-HT3a dosage response curve of Australian sandalwood extract. FIG. 6 shows the 5-HT3a dosage response curve of sandalwood oil. FIG. 7 shows the 5-HT3a dosage response curve of evodia fruit. FIG. 8 shows the 5-HT3a dosage response curve of coptis rhizome. FIG. 9 shows the 5-HT3a dosage response curve of oils from *Wisteria sinensis*. FIG. 10 shows the 5-HT3a dosage response curve of myrtle extract. FIG. 11 shows the 5-HT3a dosage response curve of wild cherry bark. FIG. 12 shows the 5-HT3a dosage response curve of Chinese Agarwood resinous heartwood extract. FIG. 13 shows the 5-HT3a dosage response curve of ginger root. FIG. 14 shows the 5-HT3a dosage response curve of marigold. FIG. 15 shows the 5-HT3a dosage response curve of boswellia. FIG. 16 shows the 5-HT3a dosage response curve of frankincense oil. FIG. 17 shows the 5-HT3a dosage response curve of prickly ash fruit. FIG. 18 shows the 5-HT3a dosage response curve of *Pinus pinaster* bark extract. FIG. 19 shows the 5-HT3a dosage response curve of horehound. FIG. 20 shows the 5-HT3a dosage response curve of bitter orange fruit. FIG. 21 shows the 5-HT3a dosage response curve of angelica. FIG. 22 shows the 5-HT3a dosage response curve of coconut oil. FIG. 23 shows the 5-HT3a dosage response curve of Chinese rose. FIG. 24 shows the 5-HT3a dosage response curve of cinnamon. FIG. 25 shows the 5-HT3a dosage response curve of bilberry. FIG. 26 shows the 5-HT3a dosage response curve of blueberry leaf. FIG. 27 shows the 5-HT3a dosage response curve of carrot extract. FIG. 28 shows the 5-HT3a dosage response curve of chamomile. FIG. 29 shows the 5-HT3a dosage response curve of turmeric. FIG. 30 shows the 5-HT3a dosage response curve of cranberry. FIG. 31 shows the 5-HT3a dosage response curve of flax oil powder. FIG. 32 shows the 5-HT3a dosage response curve of Japanese Raisin tree seed extract. FIG. 33 shows the 5-HT3a dosage response curve of andrographis herb. FIG. 34 shows the 5-HT3a dosage response curve of bee pollen. FIG. 35 shows the 5-HT3a dosage response curve of Australian eucalyptus extract. FIG. 36 shows the 5-HT3a dosage response curve of *Yerba santa*. FIG. 37 shows the 5-HT3a dosage response curve of black pepper oil. FIG. 38 shows the 5-HT3a dosage response curve of *ginkgo biloba*. FIG. 39 shows the 5-HT3a dosage response curve of cayenne.

Figure 40:
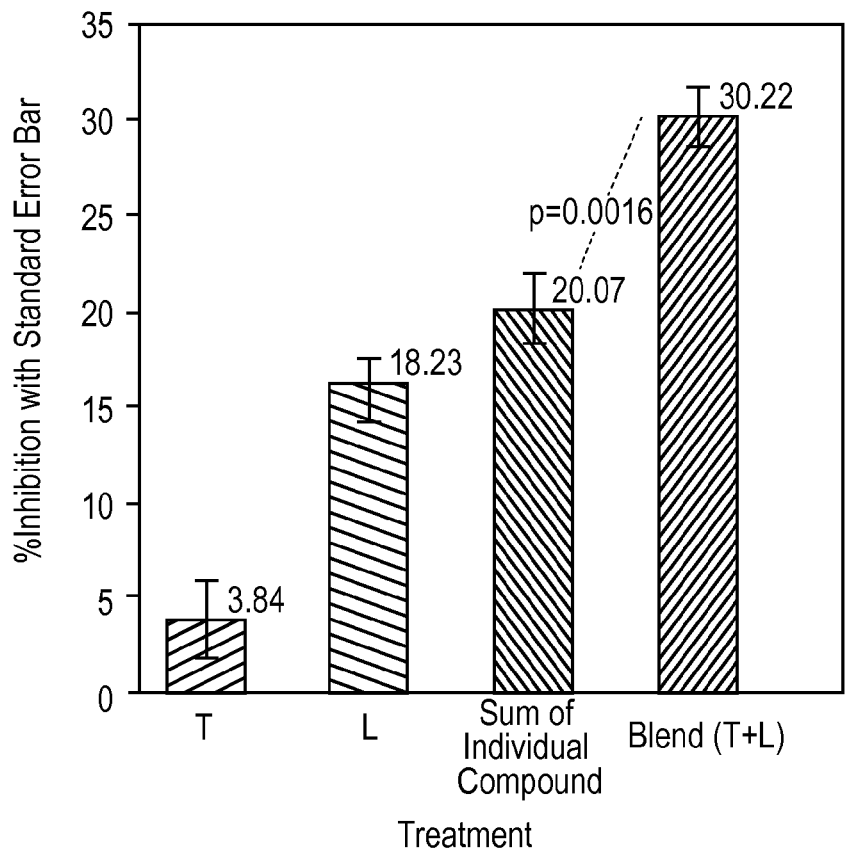
FIGS. 40 to 44 are graphs showing the unexpected synergistic 5-HT3a inhibitory effect achieved by certain combinations of plant materials or extracts, as discovered by inventors of the present invention.
Figure 41:
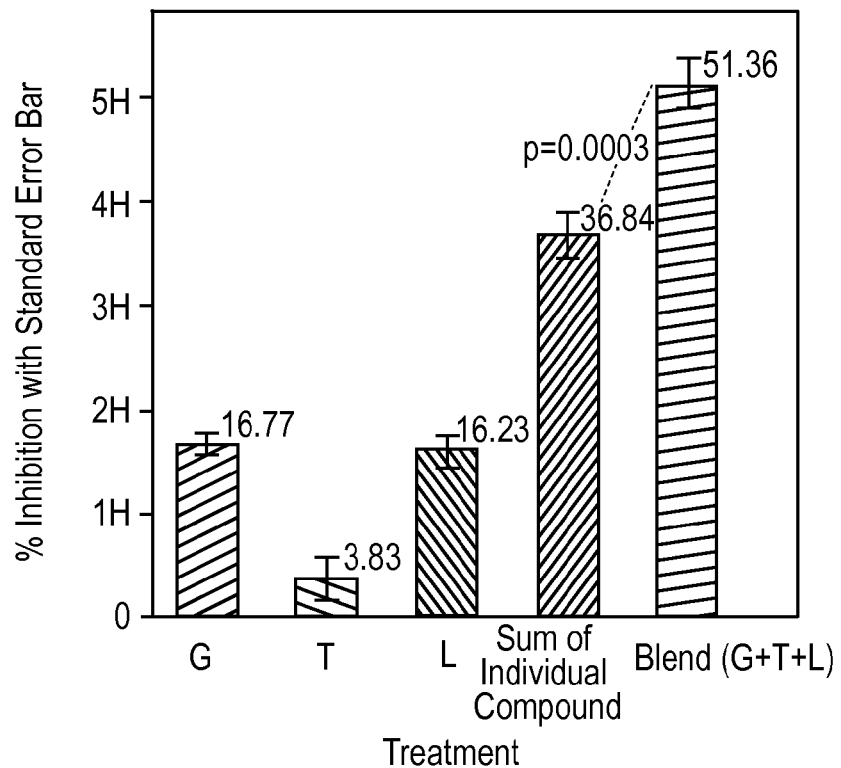
Figure 42:
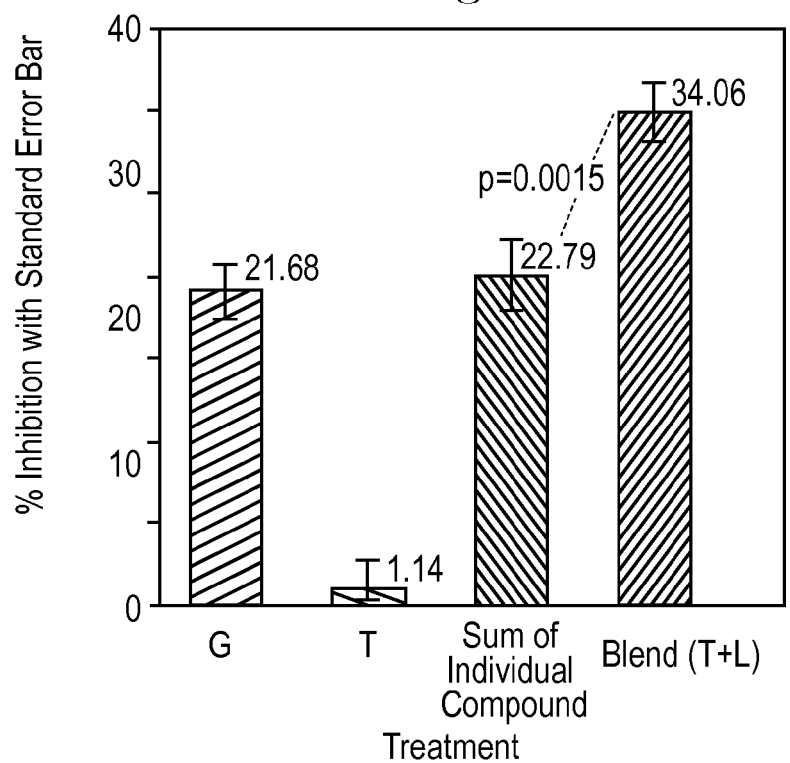
Figure 43:
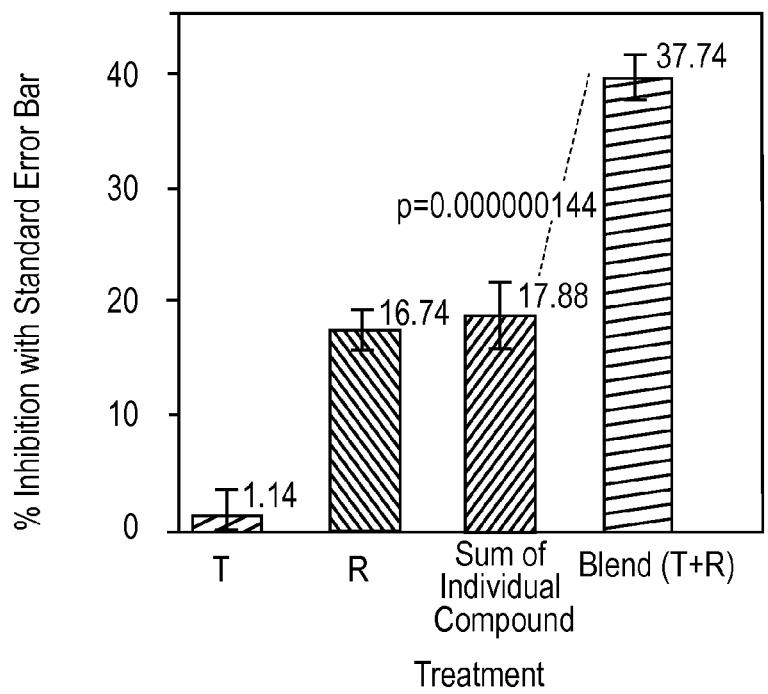
Figure 44:
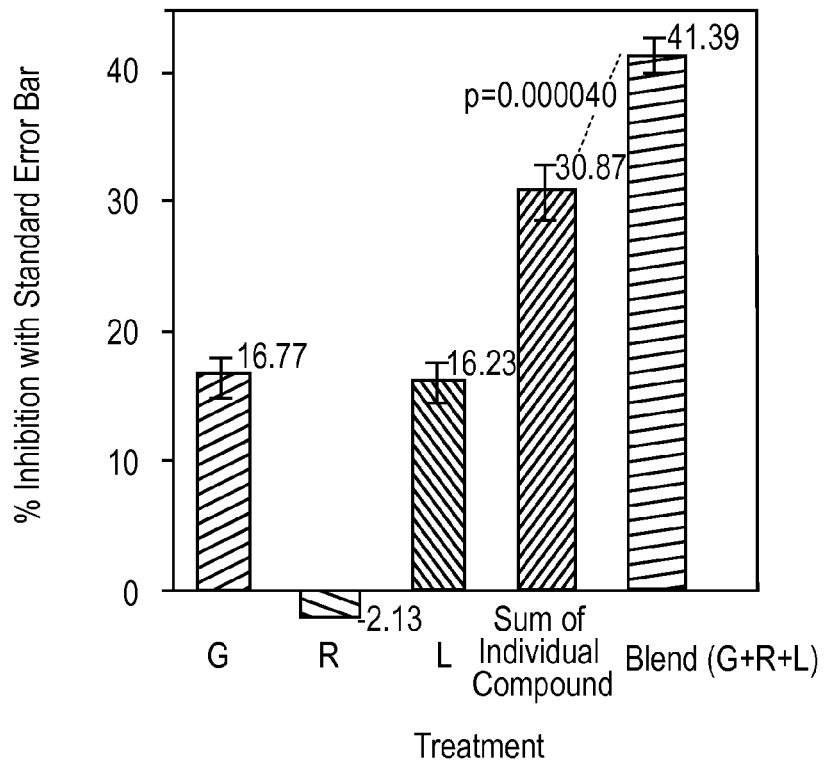

Further, FIGS. 40-44 are graphs showing the synergistic 5-HT3a inhibitory effect achieved by certain combinations of plant materials or extracts as described hereinabove. Specifically, FIG. 40 shows the combined 5-HT3a inhibitory effect achieved by the combination of turmeric (T) and licorice (L), which is larger than the sum of the 5-HT3a inhibitory effects achieved separately by turmeric and licorice. FIG. 41 shows the combined 5-HT3a inhibitory effect achieved by the combination of turmeric (T), licorice (L) and ginger (G), which is larger than the sum of the 5-HT3a inhibitory effects achieved separately by turmeric, licorice and ginger. FIG. 42 shows the combined 5-HT3a inhibitory effect achieved by the combination of turmeric (T) and ginger (G), which is larger than the sum of the 5-HT3a inhibitory effects achieved separately by turmeric and ginger. FIG. 43 shows the combined 5-HT3a inhibitory effect achieved by the combination of turmeric (T) and rhubarb (R), which is larger than the sum of the 5-HT3a inhibitory effects achieved separately by turmeric and rhubarb. FIG. 44 shows the combined 5-HT3a inhibitory effect achieved by the combination of licorice (L), ginger (G) and rhubarb (R), which is larger than the sum of the 5-HT3a inhibitory effects achieved separately by licorice, ginger and rhubarb.

Assays for Screening Nk-1 Receptor Inhibitors

Various known high through-put screening assays can also be used to determine the inhibitory effects of a material on the NK-1 receptors.

One exemplary assay is the Tango™ G-Protein Coupled Receptors (GPCR) cell-based assays by Invitrogen. First, TACR1-bla U2OS cells (from Invitrogen) are cultured in McCoy's medium. The cultured cells are then plated in DMEM into 96-well plates (15,125 cells/well in 90 uL/well). After 16-24 hours, the cells are treated with test materials or positive control antagonist (which is 100 nM Aprepitant) and then incubated for 30-60 minutes at 37° C. in 5% $CO_2$. Subsequently, the cells are treated with 1 nM SAR9 Substance P agonist and incubated again for 5 hours at 37° C. in 5% $CO_2$. The plates are removed from the incubator and equilibrated at room temperature for 15 minutes. During the equilibration step, the LiveBlazer substrate detection solution (from Invitrogen) is prepared. Six times of substrate mixture is added to each well, followed by incubating the plates in the dark at room temp for 2 hours. The plates are read by the Envision microplate reader in 2 channels using the "Geneblazer 451" protocol, which include a blue channel (Excitement at 405 and Emission at 460) and a green channel (Excitement at 405 and Emission at 535).

Figure 45:
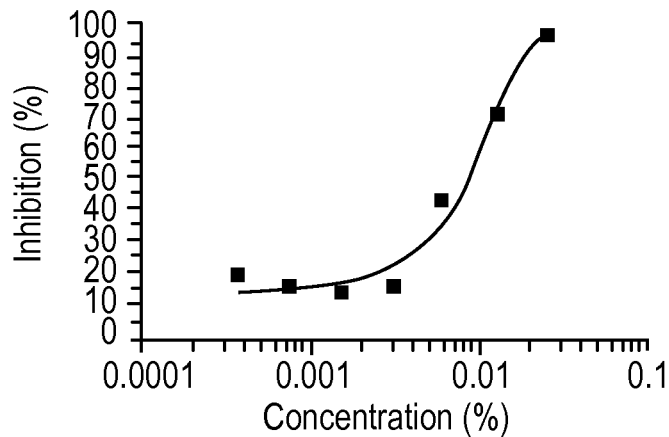
FIGS. 45 to 64 show the NK-1 dosage response curves of plant materials and extracts of the present invention with surprisingly high NK-1 inhibitory effect.
Figure 46:
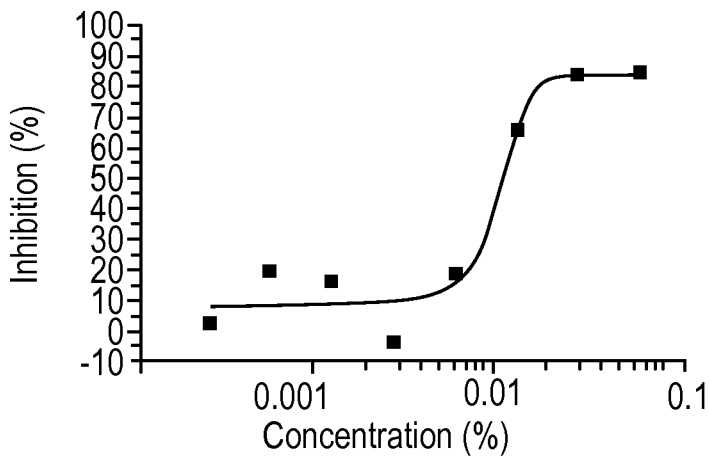
Figure 47:
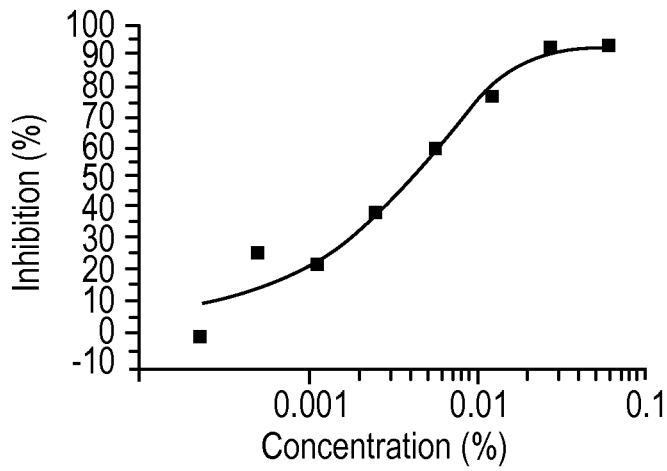
Figure 48:
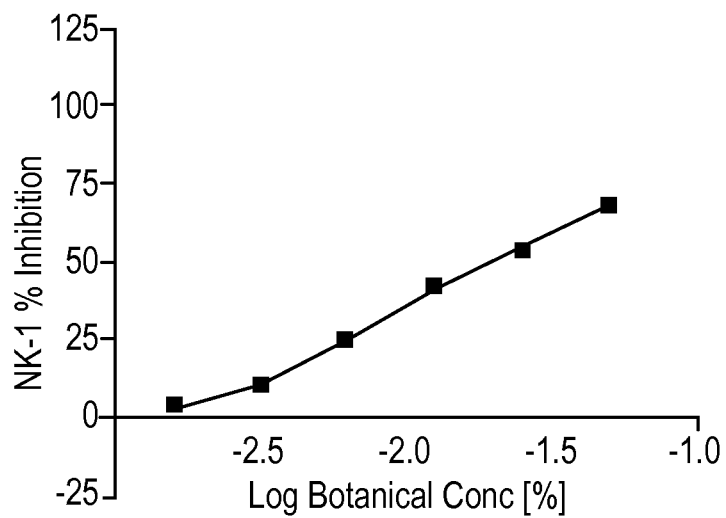
Figure 49:
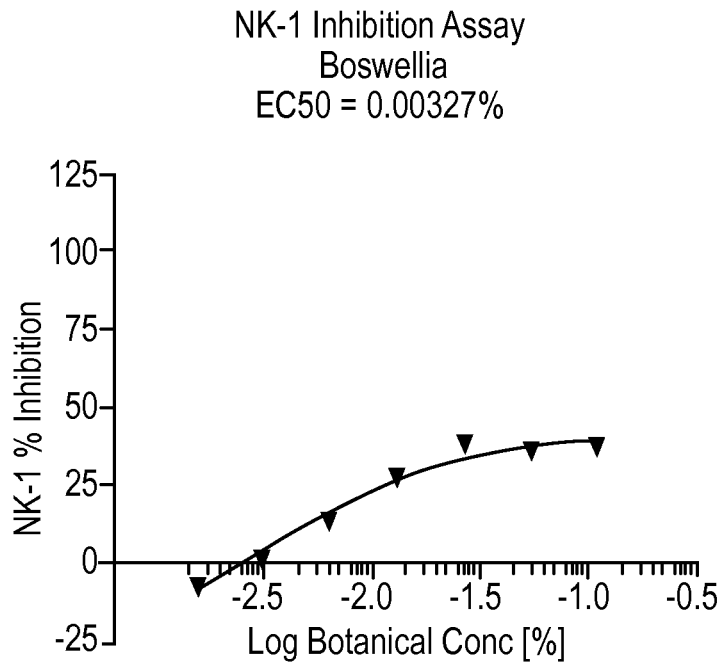
Figure 50:
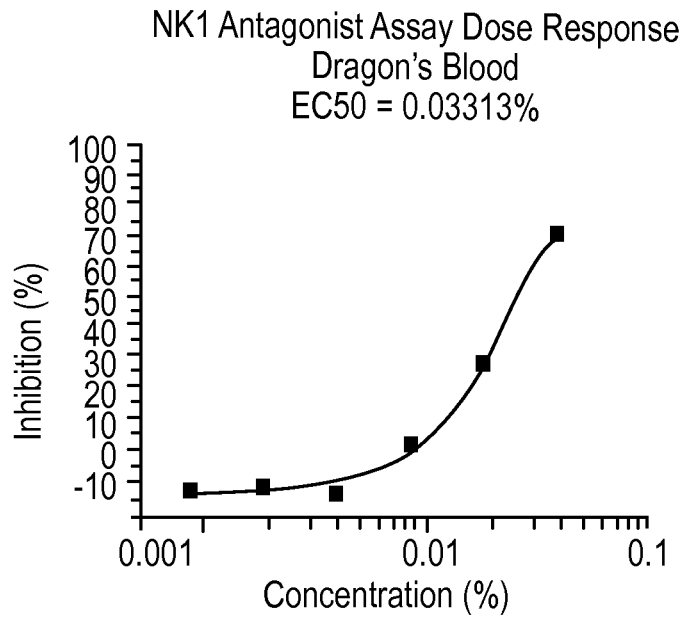
Figure 51:
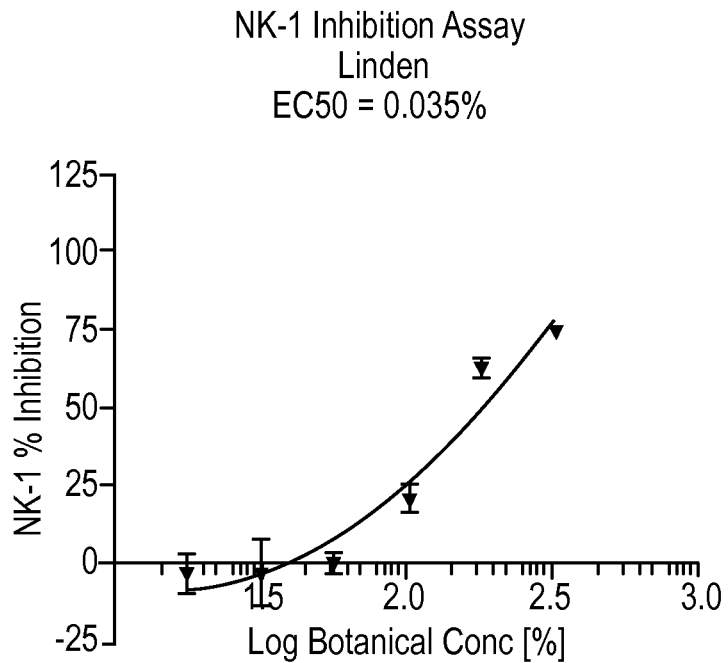
Figure 52:
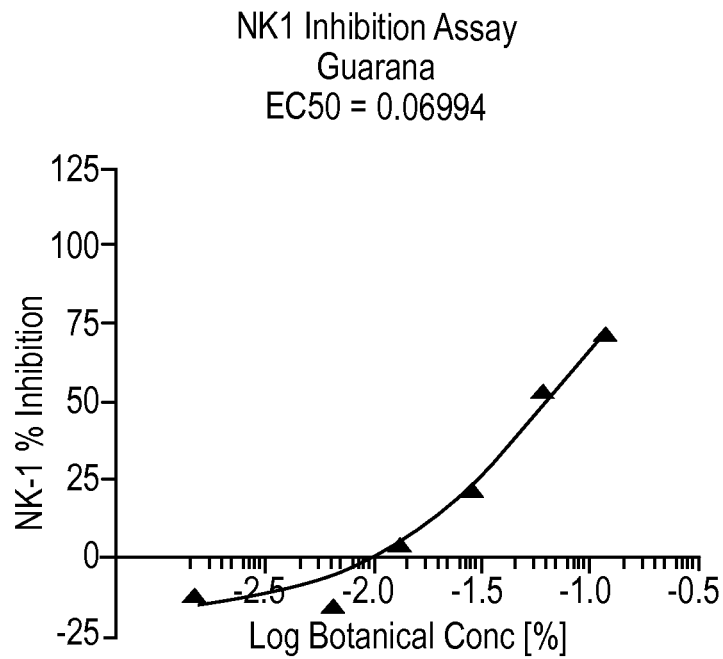
Figure 53:
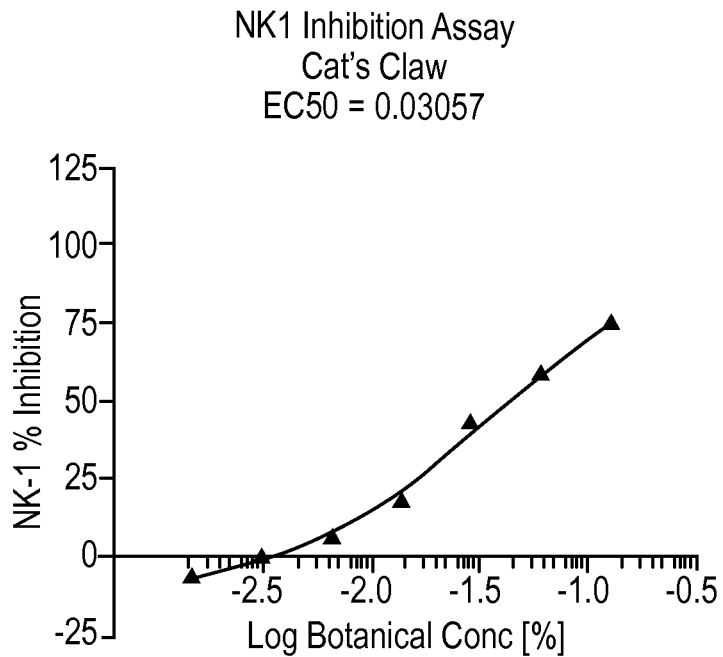
Figure 54:
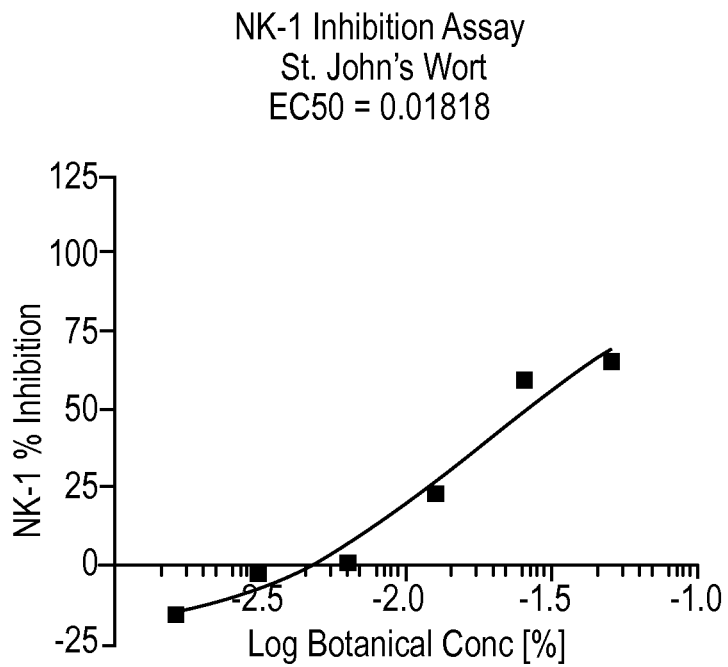
Figure 55:
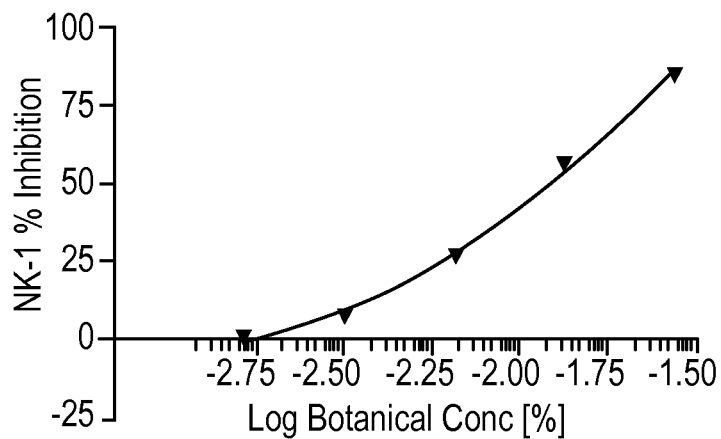
Figure 56:
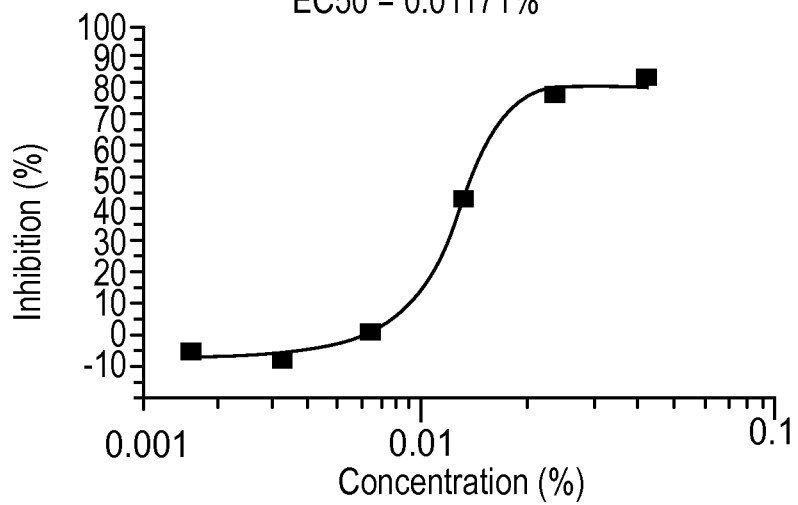
Figure 57:
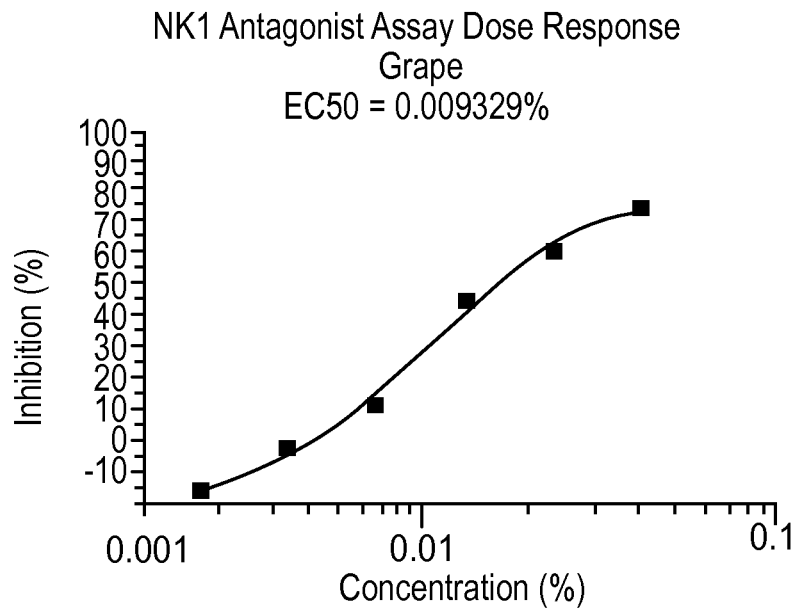
Figure 58:
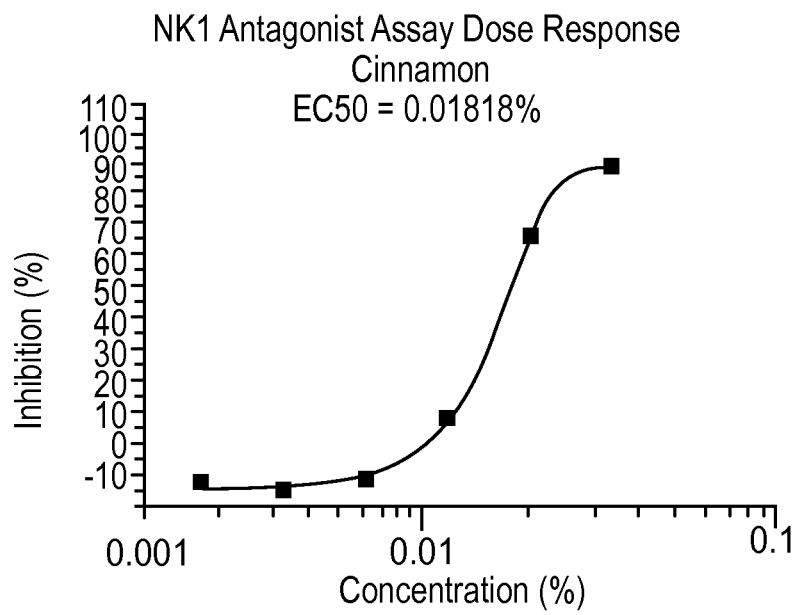
Figure 59:
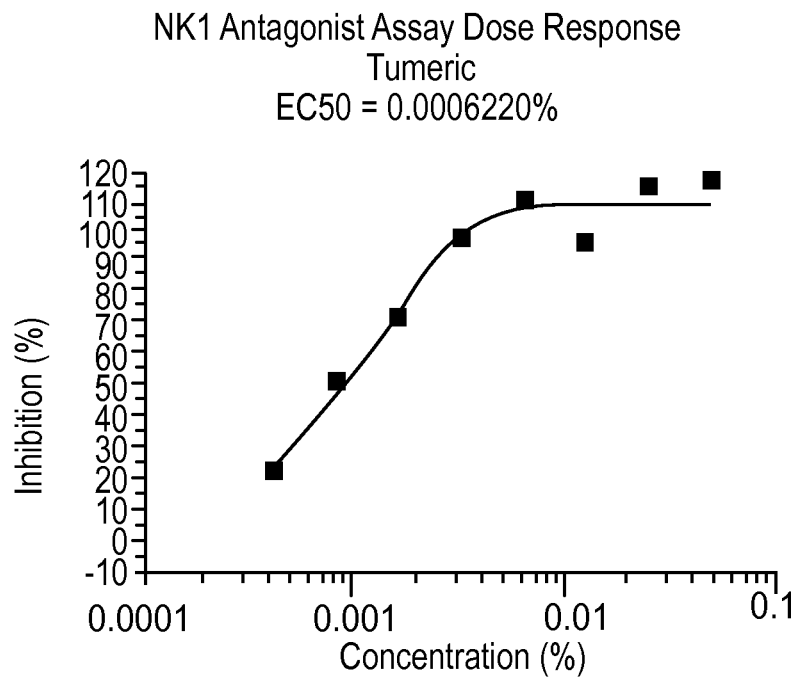
Figure 60:
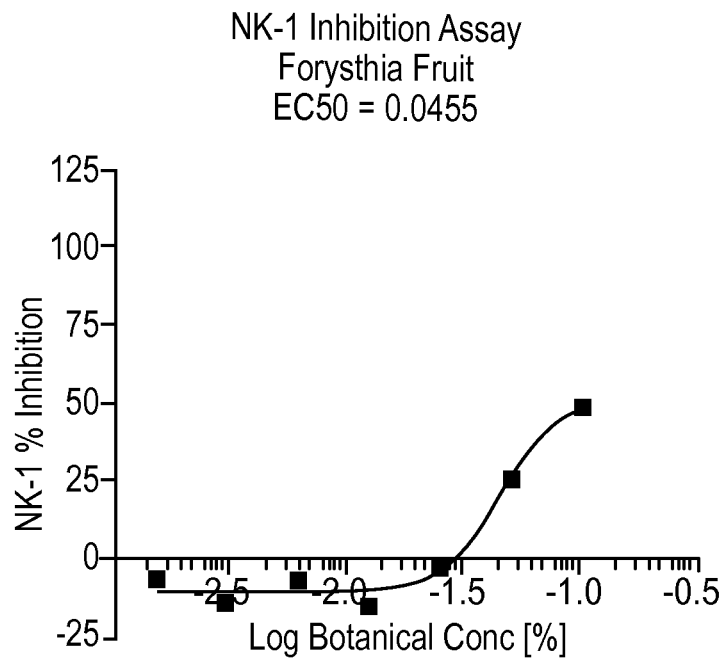
Figure 61:
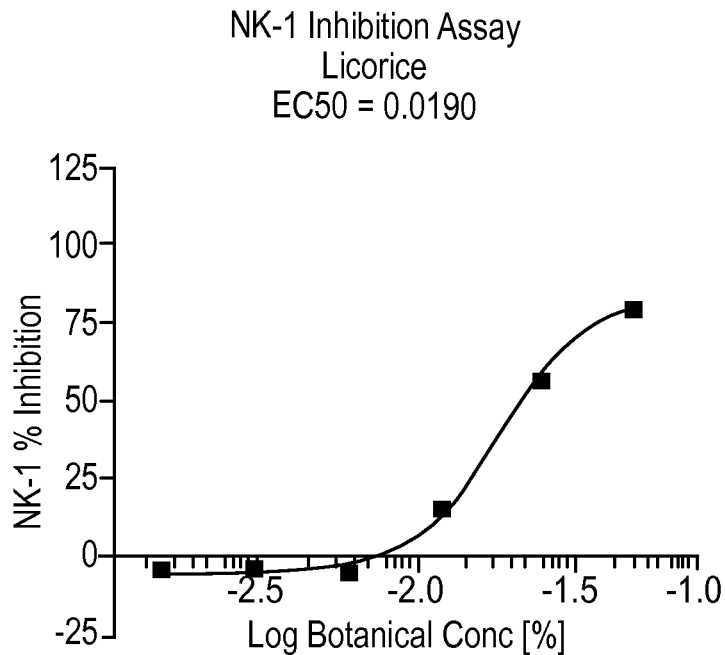
Figure 62:
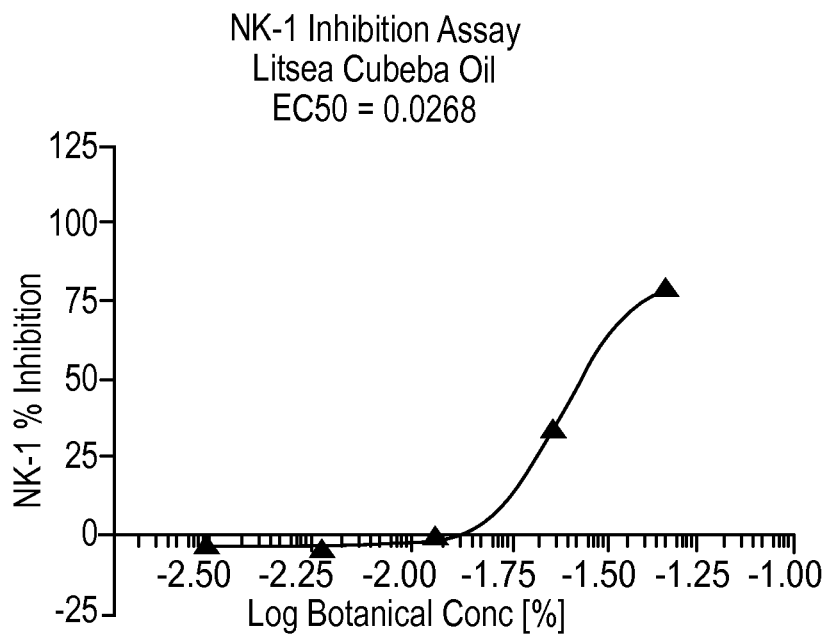
Figure 63:
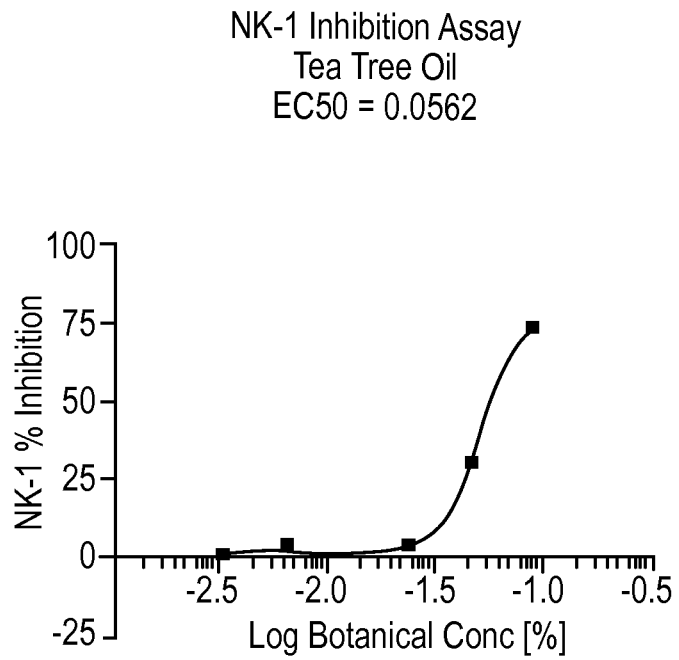
Figure 64:
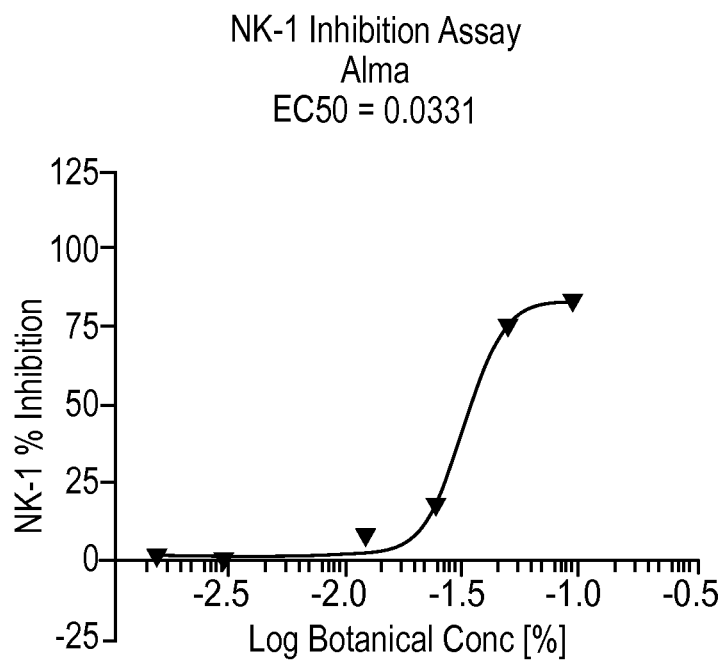

FIGS. 45 to 64 show the NK-1 dosage response curves of plant materials and extracts described hereinabove with high NK-1 inhibitory effect. Specifically, FIG. 45 shows the NK-1 dosage response curve of podophyllin. FIG. 46 shows the NK-1 dosage response curve of rhodiola. FIG. 47 shows the NK-1 dosage response curve of feverfew. FIG. 48 shows the NK-1 dosage response curve of pink bark. FIG. 49 shows the NK-1 dosage response curve of boswellia. FIG. 50 shows the NK-1 dosage response curve of dragon's blood. FIG. 51 shows the NK-1 dosage response curve of linden. FIG. 52 shows the NK-1 dosage response curve of guarana. FIG. 53 shows the NK-1 dosage response curve of cat's claw. FIG. 54 shows the NK-1 dosage response curve of St. John's wort. FIG. 55 shows the NK-1 dosage response curve of calendula. FIG. 56 shows the NK-1 dosage response curve of green tea. FIG. 57 shows the NK-1 dosage response curve of grape extract. FIG. 58 shows the NK-1 dosage response curve of cinnamon. FIG. 59 shows the NK-1 dosage response curve of turmeric. FIG. 60 shows the NK-1 dosage response curve of forsythia fruit. FIG. 61 shows the NK-1 dosage response curve of licorice. FIG. 62 shows the NK-1 dosage response curve of Litsea cubeba oil. FIG. 63 shows the NK-1 dosage response curve of tea tree oil. FIG. 64 shows the NK-1 dosage response curve of amla.

Figure 65:
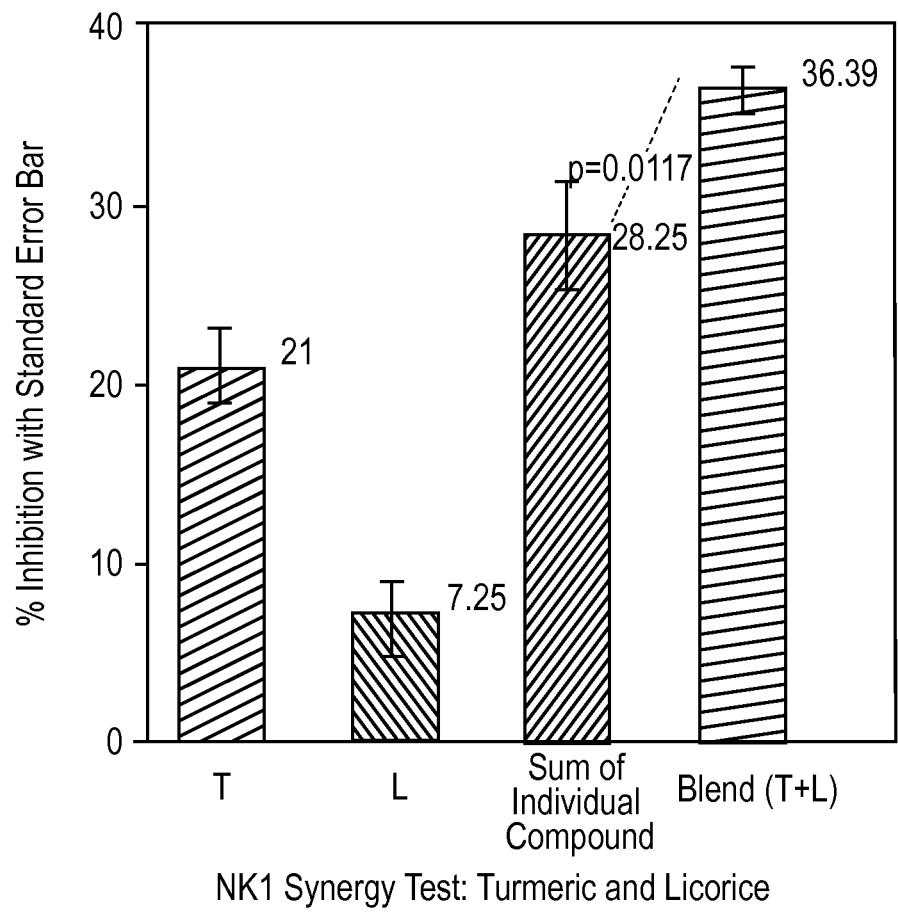
FIG. 65 is a graph showing the unexpected synergistic NK-1 inhibitory effect achieved by a specific combination of plant materials or extracts, as discovered by inventors of the present invention.

Further, FIG. 65 shows the synergistic NK-1 inhibitory effect achieved by certain combinations of plant materials or extracts as described hereinabove. Specifically, FIG. 65 shows the combined NK-1 inhibitory effect achieved by the combination of turmeric (T) and licorice (L), which is larger than the sum of the NK-1 inhibitory effects achieved separately by turmeric and licorice.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for treating idiopathic vomiting in a companion animal, comprising the step of orally administering to said companion animal one or more plant materials or extracts thereof in an effective amount for inhibiting a 5-hydroxytryptamine-3a serotonin (5-HT3a) receptor and/or a neurokinin-1 (NK-1) receptor, wherein the one or more plant materials or extracts thereof consists of Curcuma longa (turmeric) and licorice, ginger, rhubarb, or a combination thereof.

2. The method of claim 1, wherein said plant materials or extracts are orally administered to the companion animal as a part of a dietary composition.

3. The method of claim 2, wherein said dietary composition is a pet food comprising from 0.1 ppm to 75,000 ppm of said plant materials or extracts thereof, and wherein said pet food further comprises a source of carbohydrate, a source of protein, and optionally a source of fat.

4. The method of claim 2, wherein said dietary composition is a pet food supplement comprising from 0.1% to 99% of said plant materials or extracts thereof by weight, and wherein the step of orally administering comprises feeding the pet food supplement to the companion animal either separately from or in combination with a pet food.

5. The method of claim 2, wherein said dietary composition is orally administered to the companion animal at a frequency ranging from once a month to six times a day.

6. The method of claim 2, wherein said dietary composition is orally administered to the companion animal for a duration ranging from five days to twenty five years.

* * * * *